(12) United States Patent
Carter et al.

(10) Patent No.: US 10,986,838 B2
(45) Date of Patent: *Apr. 27, 2021

(54) HERBICIDES

(71) Applicant: SYNGENTA PARTICIPATIONS AG, Basel (CH)

(72) Inventors: Neil Brian Carter, Bracknell (GB); Emma Briggs, Bracknell (GB); Kenneth Ling, Bracknell (GB); James Alan Morris, Bracknell (GB); Melloney Morris, Bracknell (GB); Jeffrey Steven Wailes, Bracknell (GB); John Williams, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 141 days.

This patent is subject to a terminal disclaimer.

(21) Appl. No.: 16/087,071

(22) PCT Filed: Mar. 16, 2017

(86) PCT No.: PCT/EP2017/056283
§ 371 (c)(1),
(2) Date: Sep. 20, 2018

(87) PCT Pub. No.: WO2017/162521
PCT Pub. Date: Sep. 28, 2017

(65) Prior Publication Data
US 2019/0327972 A1    Oct. 31, 2019

(30) Foreign Application Priority Data

Mar. 23, 2016  (GB) .................................. 1604969.4

(51) Int. Cl.
| | | |
|---|---|---|
| *A01N 43/54* | (2006.01) | |
| *A01N 43/40* | (2006.01) | |
| *A01N 43/56* | (2006.01) | |
| *A01N 43/60* | (2006.01) | |
| *A01N 43/76* | (2006.01) | |
| *A01N 43/78* | (2006.01) | |
| *A01N 43/84* | (2006.01) | |

(52) U.S. Cl.
CPC .............. *A01N 43/54* (2013.01); *A01N 43/40* (2013.01); *A01N 43/56* (2013.01); *A01N 43/60* (2013.01); *A01N 43/76* (2013.01); *A01N 43/78* (2013.01); *A01N 43/84* (2013.01)

(58) Field of Classification Search
None
See application file for complete search history.

(56) References Cited

U.S. PATENT DOCUMENTS

| 2013/0005574 A1 | 1/2013 | Epp et al. |
| 2014/0274703 A1 | 9/2014 | Eckelbarger et al. |

FOREIGN PATENT DOCUMENTS

| JP | 2014208631 A | 11/2014 |
| RU | 2065861 C1 | 8/1996 |
| WO | 2009/138712 A2 | 11/2009 |
| WO | 2015/052076 A1 | 4/2015 |

OTHER PUBLICATIONS

Nantka-Nannirski et al (Acta Poloniae Pharmaceutica 34:133-138, 1977 (Year: 1977).*
International Search Report of International Patent Application No. PCT/EP2017/056283 dated May 16, 2017.
Great Britain Search Report for priority application No. GB1604969.4 dated Jan. 5, 2017.
Niantka-Namirski et al; Bipyridyls IX Synthesis and reactions of 2-hydroxy-6-pyridylnicotinic acid derivatives; Acta Poloniae Pharmaceutica, vol. 34, No. 2, 1977 (pp. 133-138), *Compounds only.
Harcken et al., Identification of Highly Efficacious Glucocorticoid Receptor Agonists with a Potential for Reduced Clinical Bone Side Effects, Journal of Medicinal Chemistry, 2014, 57 (pp. 1583-1598).
"Compound Summary for CID 114049669"; Pubchem Compound Database, Jan. 28, 2016.
"Compound Summary for CID 114049670"; Pubchem Compound Database, Jan. 28, 2016.
"Compound Summary for CID 118174153"; Pubchem Compound Database, Feb. 23, 2016.
"Compound Summary for CID 118560778"; Pubchem Compound Database, Feb. 23, 2016.
Database Registry (online); Chemical Abstracts Service, Columbus, Ohio, US; Mar. 4, 2016, XP002769507, Database Accession No. 1879169-89-7.
Database Registry (online); Chemical Abstracts Service, Columbus, Ohio, US; Feb. 4, 2016, XP002769508, Database Accession No. 1859450-36-4.
Database Registry (online); Chemical Abstracts Service, Columbus, Ohio, US; May 20, 2015, XP002769509, Database Accession No. 1708288-65-6.

* cited by examiner

*Primary Examiner* — Craig D Ricci
(74) *Attorney, Agent, or Firm* — Baker & Hostetler LLP; Toni-Junell Herbert

(57) ABSTRACT

The present invention relates to herbicidally active pyridino-/pyrimidino-pyridine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

16 Claims, No Drawings

HERBICIDES

CROSS-REFERENCE TO RELATED APPLICATIONS

This application is a 371 National Stage application of International Application No. PCT/EP2017/056283, filed Mar. 16, 2017, which claims priority to Great Britain Patent Application No. 1604969.4 filed Mar. 23, 2016, the entire contents of which applications are hereby incorporated by reference.

The present invention relates to herbicidally active pyridino-/pyrimidino-pyridine derivatives, as well as to processes and intermediates used for the preparation of such derivatives. The invention further extends to herbicidal compositions comprising such derivatives, as well as to the use of such compounds and compositions in controlling undesirable plant growth: in particular the use in controlling weeds, in crops of useful plants.

Certain pyrido-pyridine and pyrimidino-pyridine derivatives are known from JP2014-208631, where they are stated to have activity as insecticidal agents, and in particular miticidal agents.

The present invention is based on the finding that pyridino-pyridine, and pyrimidino-pyridine, derivatives of Formula (I) as defined herein, exhibit surprisingly good herbicidal activity. Thus, in a first aspect of the invention there is provided the use of a compound of formula (I)

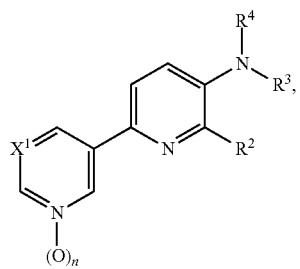

(I)

$X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-C$_6$alkyl, —S(O)$_p$C$_1$-C$_6$alkyl, NR$^6$R$^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-C$_6$alkyl, —S(O)$_p$(C$_1$-C$_6$alkyl), $C_1$-$C_6$alkoxy, $C_1$-$C_6$haloalkoxy and phenyl;

$R^3$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^a$ is hydrogen or $C_1$-$C_2$ alkyl;

$R^b$ is hydrogen or $C_1$-$C_2$ alkyl;

$R^4$ is hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^5$ is —C(O)OC$_1$-C$_6$alkyl, —C$_3$-C$_{10}$cycloalkyl, -aryl, or -heteroaryl wherein said aryl and heteroaryl are optionally substituted by 1 to 3 independent $R^8$;

or $R^3$ and $R^4$ together with the nitrogen to which they are attached, form a saturated or partially unsaturated 4-6 membered ring system optionally containing 1 or 2 further heteroatoms independently selected from S, O and N, wherein said ring is optionally substituted by 1 to 3 $R^8$;

$R^6$ and $R^7$ are independently selected from the group consisting of hydrogen, $C_1$-$C_6$alkyl and —C(O)OC$_1$-C$_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and S(O)$_p$(C$_1$-C$_6$alkyl);

n is 0 or 1;

p is 0, 1, or 2; and q is 0, 1, or 2, as a herbicide.

Certain compounds of formula (I) are novel. Thus, in a second aspect the invention provides a compound of Formula (I)

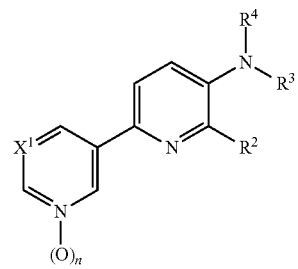

(I)

or a salt thereof, wherein:

$X^1$ is N or $CR^1$;

$R^1$ is selected from the group consisting of hydrogen, halogen, cyano, $C_1$-$C_6$alkyl, $C_3$-$C_6$cycloalkyl, $C_2$-$C_6$alkenyl, $C_2$-$C_6$alkynyl, $C_1$-$C_6$alkoxy, —C(O)OC$_1$-C$_6$alkyl, —S(O)$_p$C$_1$-C$_6$alkyl, NR$^6$R$^7$, $C_1$-$C_6$haloalkoxy and $C_1$-$C_6$haloalkyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-C$_6$alkyl, —S(O)$_p$(C$_1$-C$_6$alkyl), $C_1$-$C_6$alkoxy, $C_1$-$C_6$haloalkoxy and phenyl;

$R^3$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^a$ is hydrogen or $C_1$-$C_2$ alkyl;

$R^b$ is hydrogen or $C_1$-$C_2$ alkyl;

$R^4$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^5$ is —C(O)OC$_1$-C$_6$alkyl, —C$_3$-C$_{10}$cycloalkyl, -aryl and -heteroaryl wherein said aryl and heteroaryl are optionally substituted by 1 to 3 independent $R^8$;

or $R^3$ and $R^4$ together with the nitrogen to which they are attached, form a saturated or partially unsaturated 4-6 membered ring system optionally containing 1 or 2 further heteroatoms independently selected from S, O and N, wherein said ring is optionally substituted by 1 to 3 $R^8$;

$R^6$ and $R^7$ are independently selected from the group consisting of hydrogen and $C_1$-$C_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and $S(O)_p(C_1$-$C_6$alkyl);

n is 0 or 1;
p is 0, 1, or 2; and
q is 0, 1, or 2;
with the proviso that:
(a) $R^3$ and $R^4$ are not both H, when $R^2$ is methyl, n is 0, and X is N or $CR^1$ when $R^1$ is methoxy, H, fluoro, cyano or methyl; and
(b) the compound of formula (I) is not (i) 2-chloro-6-(3-pyridyl)pyridine-3-amine, (ii) 2-fluoro-6-(3-pyridyl)pyridine-3-amine, (iii) 2-(difluoromethyl)-6-(3-pyridyl)pyridin-3-amine, or (iv) tert-butyl-N-[2-methyl-6-(3-pyridyl)-3-pyridyl]-carbamate.

Compounds of formula (I) may exist as different geometric isomers, or in different tautomeric forms. This invention covers the use of all such isomers and tautomers, and mixtures thereof in all proportions, as well as isotopic forms such as deuterated compounds.

It may be the case that compounds of formula (I) may contain one or more asymmetric centers and may thus give rise to optical isomers and diastereomers. While shown without respect to stereochemistry, the present invention includes the use of all such optical isomers and diastereomers as well as the racemic and resolved, enantiomerically pure R and S stereoisomers and other mixtures of the R and S stereoisomers and agrochemically acceptable salts thereof.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$ alkyl groups (except where already defined more narrowly), but are preferably $C_1$-$C_4$ alkyl or $C_1$-$C_3$ alkyl groups, and, more preferably, are $C_1$-$C_2$ alkyl groups (such as methyl).

Alkenyl and alkynyl moieties can be in the form of straight or branched chains, and the alkenyl moieties, where appropriate, can be of either the (E)- or (Z)-configuration. Alkenyl and alkynyl moieties can contain one or more double and/or triple bonds in any combination; but preferably contain only one double bond (for alkenyl) or only one triple bond (for alkynyl).

The alkenyl or alkynyl moieties are typically $C_2$-$C_4$ alkenyl or $C_2$-$C_4$ alkynyl, more specifically ethenyl (vinyl), prop-2-enyl, prop-3-enyl (allyl), ethynyl, prop-3-ynyl (propargyl), or prop-1-ynyl. Preferably, the term cycloalkyl refers to cyclopropyl, cyclobutyl, cyclopentyl or cyclohexyl.

In the context of the present specification the term "aryl" preferably means phenyl.

Heteroaryl groups and heteroaryl rings (either alone or as part of a larger group, such as heteroaryl-alkyl-) are ring systems containing at least one heteroatom and can be in mono- or bi-cyclic form. Preferably, single rings will contain 1, 2 or 3 ring heteroatoms selected independently from nitrogen, oxygen and sulfur. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$ alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$ alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$ alkyl-$S(O)_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Compounds of formula (I) may form, and/or be used as, agronomically acceptable salts with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used in salt formation, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

Compounds of formula (I) may also form (and/or be used as) agronomically acceptable salts with various organic and/or inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when the compound of formula (I) contains a basic moiety.

Where appropriate compounds of formula (I) may also be in the form of/used as an N-oxide.

Compounds of formula (I) may also be in the form of/used as hydrates which may be formed during the salt formation.

Preferred values of $X^1$, $R^1$, $R^2$, $R^3$, $R^4$, $R^5$, $R^6$, $R^7$, $R^8$, n, p and q, are as set out below, and a compound of formula (I) according to the invention may comprise any combination of said values. The skilled person will appreciate that values for any specified set of embodiments may combined with values for any other set of embodiments where such combinations are not mutually exclusive.

In one particular embodiment of the present invention, $X^1$ is N.

In another embodiment of the present invention, $X^1$ is $CR^1$ and $R^1$ is preferably selected from the group consisting of hydrogen, cyano, fluoro, chloro, methoxy, difluoromethoxy and trifluoromethyl. More preferably still, $R^1$ is selected from the group consisting of hydrogen, cyano, fluoro, chloro, methoxy and trifluoromethyl.

Preferably $R^2$ is $C_1$-$C_6$alkyl, $C_1$-$C_6$haloalkyl, cyano, —C(O)O$C_1$-$C_6$alkyl, $C_1$-$C_6$alkoxy, or phenyl. More preferably $R^2$ is $C_1$-$C_6$alkyl, $C_1$-$C_6$haloalkyl, cyano —C(O)OCH$_3$, methoxy, or phenyl. Even more preferably $R^2$ is $C_1$-$C_6$alkyl or $C_1$-$C_6$haloalkyl. More preferably still $R^2$ is methyl or trifluoromethyl.

As stated above $R^3$ and $R^4$ are each independently selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxy$C_1$-$C_3$alkyl-, $C_1$-$C_6$haloalkyl- and —$(CR^aR^b)_qR^5$.

Where $R^3$ or $R^4$ is —$(CR^aR^b)_qR^5$, it is preferred in one set of embodiments that $R^5$ is phenyl or a 5-, or 6-membered heteroaryl ring optionally substituted as described herein. More preferably $R^5$ is a phenyl, furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, or triazinyl ring, optionally substituted by 1 to 3 $R^8$ as defined herein. More preferably still, $R^5$ is a phenyl, pyridyl, pyrimidinyl, pyridazinyl, pyrazinyl, or triazinyl ring, optionally substituted by 1 to 3 $R^8$. In one set of embodiments, $R^5$ is a phenyl ring, optionally substituted by 1-3 $R^8$, in particular where q is 0 or 1.

In preferred embodiments $R^3$ is selected from the group consisting of hydrogen, $C_1$-$C_6$alkyl, $C_2$-$C_6$alkenyl, $C_2$-$C_6$alkynyl, $(CR^aR^b)_qR^5$ (in particular where $R^5$ is as preferred below). More preferably $R^3$ is selected from the group consisting of hydrogen, $C_1$-$C_6$alkyl, $C_2$-$C_6$alkenyl, $C_2$-$C_6$alkynyl, phenyl, benzyl, —(CH$_2$)C$_3$-C$_{10}$cycloalkyl, —CH(CH$_3$)phenyl, —CH$_2$C(O)OC$_1$-C$_6$alkyl and —CH(CH$_3$)C(O)OC$_1$-C$_6$alkyl wherein said benzyl and phenyl are optionally substituted by one or more (preferably from one to three e.g. one, two or three) independent $R^8$. Even more preferably $R^3$ is selected from the group consisting of hydrogen, methyl, -allyl, -but-2-ynyl, —CH$_2$CO$_2$CH$_3$, —CH(CH$_3$)C(O)OCH$_3$, —(CH$_2$)-cPr, phenyl, benzyl and —CH(CH$_3$)phenyl wherein the benzyl and phenyl are optionally substituted by one or two substituents selected from the group consisting of —CF$_3$, F, Cl and MeO—.

Preferably $R^4$ is hydrogen.

Preferably $R^5$ is $C_3$-$C_6$cycloalkyl, phenyl or a 5-10-membered heteroaryl ring system, optionally substituted as described herein. More preferably $R^5$ is a phenyl, furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, pyrazolopyridinyl, or triazinyl ring system, optionally substituted by 1 to 3 $R^8$ as defined herein. In one set of embodiments $R^5$ is a phenyl, pyridyl, pyrimidinyl, pyridazinyl, pyrazinyl, or triazinyl ring, optionally substituted by 1 to 3 $R^8$, more preferably $R^5$ is a phenyl ring, optionally substituted by 1-3 $R^8$, in particular where q is 0 or 1. In a further set of embodiments, $R^5$ is a phenyl, thiazolyl, pyrazolyl, oxazolyl or pyrazolopyridinyl ring system optionally substituted by 1-3 $R^8$.

In one particular embodiment $R^6$ and $R^7$ are both hydrogen. In another embodiment $R^6$ is hydrogen and $R^7$ is $C_1$-$C_6$alkyl (e.g., methyl or ethyl). In another embodiment, $R^6$ and $R^7$ are both $C_1$-$C_6$alkyl.

In an alternative embodiment of the present invention, $R^3$ and $R^4$ together with the nitrogen atom to which they are joined, form a saturated or partially unsaturated 4-, 5-, or 6-membered ring system, preferably 5- or 6-membered, more preferably 6-membered, optionally containing from 1 or 2 further heteroatoms independently selected from S, O and N, wherein said ring is optionally substituted by 1 to 3 independent $R^8$. Examples of such ring systems include pyrrolinyl, pyrrolidinyl, pyrazolinyl, pyrazolidinyl, imidazolinyl, imidazolidinyl, triazolyl, piperidyl, morpholinyl, thiomorpholinyl, and piperazinyl rings. Preferably in such embodiments, $R^3$ and $R^4$ together with the nitrogen atom to which they are joined form a pyrrolidinyl, piperidyl, morpholinyl, thiomorpholinyl, or piperazinyl ring.

As stated above, each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and $S(O)_p(C_1$-$C_6$alkyl). Preferably each $R^8$ is independently halogen, $C_1$-$C_6$ alkyl, $C_1$-$C_6$ haloalkyl or $C_1$-$C_6$ alkoxy. More preferably each $R^8$ is independently fluoro, chloro, methyl, trifluoromethyl or methoxy.

Table 1 below provides 65 specific examples of herbicidal compounds of Formula (I) for use according to the invention.

TABLE 1

Specific examples of compounds of Formula (I) for use in the invention

| Entry No | $X_1$ | $R_2$ | $R_3$ | $R_4$ |
|---|---|---|---|---|
| A1 | C—CN | CF$_3$ | CH$_3$ | H |
| A2 | C—CN | CF$_3$ | H | H |
| A3 | C—Cl | CF$_3$ | H | H |
| A4 | C—OCF$_2$H | CH$_3$ | H | H |
| A5 | C—F | CF$_3$ | CH$_3$ | H |
| A6 | C—CH$_3$ | CF$_3$ | CH$_3$ | H |
| A7 | C—CF$_3$ | CF$_3$ | CH$_3$ | H |
| A8 | C—F | CH$_3$ | H | H |
| A9 | C—F | CN | H | H |
| A10 | C—OCH$_3$ | CF$_3$ | CH$_3$ | H |
| A11 | C—H | CF$_3$ | CH$_3$ | H |
| A12 | C—CF$_3$ | CH$_3$ | H | H |
| A13 | C—OCH$_3$ | CH$_3$ | H | H |
| A14 | N | CH$_3$ | H | H |
| A15 | N | CH$_3$ | CH$_3$ | H |
| A16 | C—F | CF$_3$ | 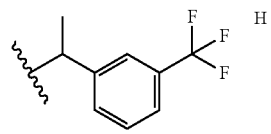 | H |
| A17 | C—F | CF$_3$ | 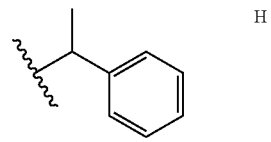 | H |
| A18 | C—F | CF$_3$ | 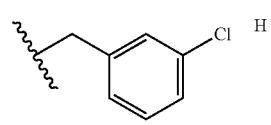 | H |
| A19 | C—F | CF$_3$ | 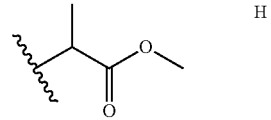 | H |

TABLE 1-continued

Specific examples of compounds of Formula (I) for use in the invention

| Entry No | $X_1$ | $R_2$ | $R_3$ | $R_4$ |
|---|---|---|---|---|
| A20 | C—F | $CF_3$ | CH₂-(4-methylphenyl) | H |
| A21 | C—F | $CF_3$ | $CH_2Ph$ | H |
| A22 | C—F | $CF_3$ | $CH_2CO_2CH_3$ | H |
| A23 | C—F | $CF_3$ | CH₂-(3-methoxyphenyl) | H |
| A24 | C—F | $CF_3$ | CH₂-(4-chlorophenyl) | H |
| A25 | C—F | $CF_3$ | CH₂CH=CH₂ (allyl-type, homoallyl) | H |
| A26 | C—F | $CF_3$ | CH₂-(4-trifluoromethylphenyl) | H |
| A27 | C—F | $CF_3$ | $CH_2CH_3$ | H |
| A28 | C—F | $CF_3$ | CH₂-(2,4-difluorophenyl) | H |
| A29 | C—F | $CF_3$ | CH₂-cyclopropyl | H |
| A30 | C—F | $CF_3$ | CH₂C≡C-CH₃ (propargyl-methyl) | H |
| A31 | C—F | $CF_3$ | CH₂-(4-fluorophenyl) | H |
| A32 | C—F | $CF_3$ | Ph | H |
| A33 | C—F | $CF_3$ | H | H |
| A34 | N | $CF_3$ | $CH_3$ | H |
| A35 | N | $CF_3$ | H | H |
| A36 | C—H | $CF_3$ | $CH_3$ | H |
| A38 | C—F | $CF_3$ | $CH_3$ | $CH_3$ |
| A39 | C—F | $CF_3$ | —CH₂CH₂OCH₂CH₂— | |
| A40 | C—F | $CF_3$ | —(CH₂)₄— | |
| A41 | C—F | $CO_2CH_3$ | H | H |
| A42 | C—F | $CF_3$ | $(CH_2)_5CH_3$ | H |
| A43 | C—F | $OCH_3$ | H | H |
| A44 | N | CN | H | H |
| A45 | C—F | $CF_3$ | cyclohexyl | H |
| A46 | C—F | $CF_3$ | cyclopropyl | H |
| A47 | C—F | $CF_3$ | $(CH_2)_2CH_3$ | H |
| A48 | C—F | $CF_3$ | $(CH_2)_2CH_3$ | $(CH_2)_2CH_3$ |
| A49 | C—F | $CF_3$ | $(CH_2)_2Ph$ | H |
| A50 | C—F | Ph | H | H |
| A51 | C—F | $CF_3$ | $CH_2$cyclobutyl | H |
| A52 | C—F | $CF_3$ | $CH_2$cyclohexyl | H |
| A53 | C—F | $CF_3$ | $(CH_3)_2CH(CH_3)_2$ | H |
| A54 | C—F | $CF_3$ | $(CH_3)_4CH_3$ | H |
| A55 | C—F | $CF_3$ | CH₂-(pyrazolo[1,5-a]pyridin-2-yl) | H |
| A56 | C—F | $CF_3$ | CH₂-(thiazol-2-yl) | H |
| A57 | C—F | $CF_3$ | CH₂-(thiazol-4-yl) | H |
| A59 | C—F | $CF_3$ | CH₂-(1-methylpyrazol-3-yl) | H |
| A60 | C—F | $CF_3$ | CH₂-(oxazol-5-yl) | H |
| A61 | C—F | $CF_3$ | —(CH₂)₂NCH₃(CH₂)₂— | |
| A62 | C—F | $CF_3$ | —CH₂(CF₂)₂CH₂— | |
| A63 | C—F | $CF_3$ | —(CH₂)₃— | |
| A64 | C—F | $CF_3$ | —CHCF₃(CH₂)₃— | |
| A65 | C—F | $CF_3$ | CH₂CH₂CH=CH₂ | CH₂CH=CH₂ |
| A66 | C—F | $CF_3$ | $CH_2CH(CH_3)_2$ | H |
| A67 | C—F | $CF_3$ | $(CH_2)_2CF_3$ | H |

Compounds of Formula (I) may be prepared according to the following schemes, in which the substituents $X^1$, $R^1$, $R^2$, $R^3$, $R^4$, $R^5$, $R^6$, $R^7$, $R^8$, $R^a$, $R^b$, n, p and q have (unless otherwise stated explicitly) the definitions described hereinbefore, using techniques known to the person skilled in the art of organic chemistry. General methods for the production of compounds of formula (I) are described below. The starting materials used for the preparation of the compounds of the invention may be purchased from the usual commercial suppliers or may be prepared by known methods. The starting materials as well as the intermediates may be purified before use in the next step by state of the art methodologies such as chromatography, crystallization, distillation and filtration.

Typical abbreviations used throughout are as follows:
Ac=acetyl
app=apparent
BINAP=2,2'-bis(diphenylphosphino)-1,1'-binaphthyl
Br. or br=broad
tBu=tert-butyl
t-BuOH=tert-butanol
d=doublet
dd=double doublet
Dba=dibenzylideneacetone
DCM=dichloromethane
DMF=N, N-dimethylformamide
DMSO=dimethylsulfoxide
DPPA=diphenylphosphoryl azide
$Et_3N$=triethylamine
$Et_2O$=diethyl ether
EtOAc=ethyl acetate
EtOH=ethanol
m=multiplet
mCPBA=meta-chloro-perbenzoic acid
Me=methyl
MeOH=methanol
Ms=mesylate
Ph=phenyl
q=quartet
RT=room temperature
s=singlet
t=triplet
Tf=triflate
TFA=trifluoroacetic acid
THF=tetrahydrofuran
TMS=tetramethylsilane
tr=retention time Processes for preparation of compounds of formula (I) (which may be in the form of an agrochemically acceptable salt thereof), are now described, and form further aspects of the present invention.

example C. Kremoser et al Bioorg. Med. Chem. Lett (2010) 4911). Suitable solvents include tetrahydrofuran or DMF. Compounds of Formula A are commercially available or can be prepared by methods well known in the literature.

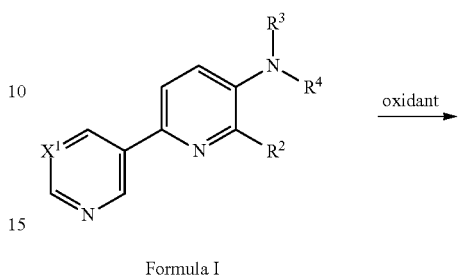

Formula I

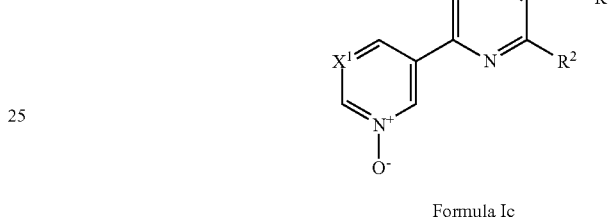

Formula Ic

A compound of Formula Ic (a compound of Formula I where n is 1) may be prepared from a compound of Formula I (where n is 0) via reaction with a suitable oxidant in a suitable solvent. Suitable oxidants may include 3-chloroperbenzoic acid (see for example UCB Pharma WO2012032334). Suitable solvents may include DCM.

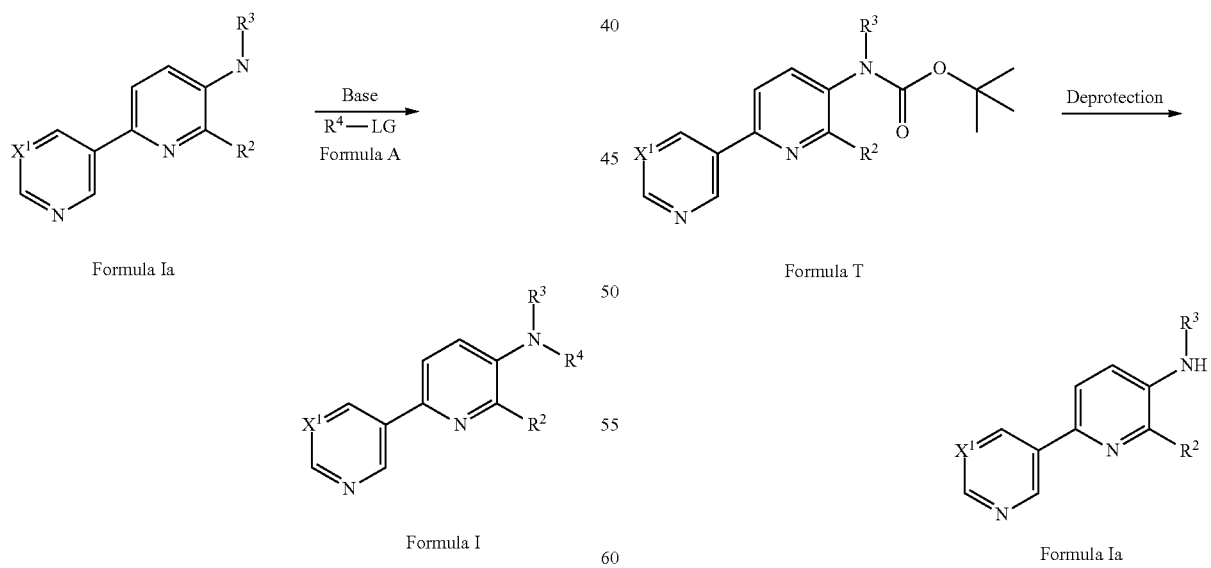

A compound of Formula I (where either $R^3$ and/or $R^4$ is not/are not hydrogen) can be prepared from a compound of Formula Ia via an alkylation reaction with a compound of Formula A (where LG is a suitable leaving group, such as Br, I or OMs) in the presence of a suitable base and in a suitable solvent. Suitable bases include sodium hydride (see for A compound of Formula Ia (i.e. a compound of Formula I where $R^4$ is hydrogen) may be prepared from a compound of Formula T via a deprotection reaction using a suitable reagent in a suitable solvent. Suitable reagents may include trifluoroacetic acid. Suitable solvents may include DCM.

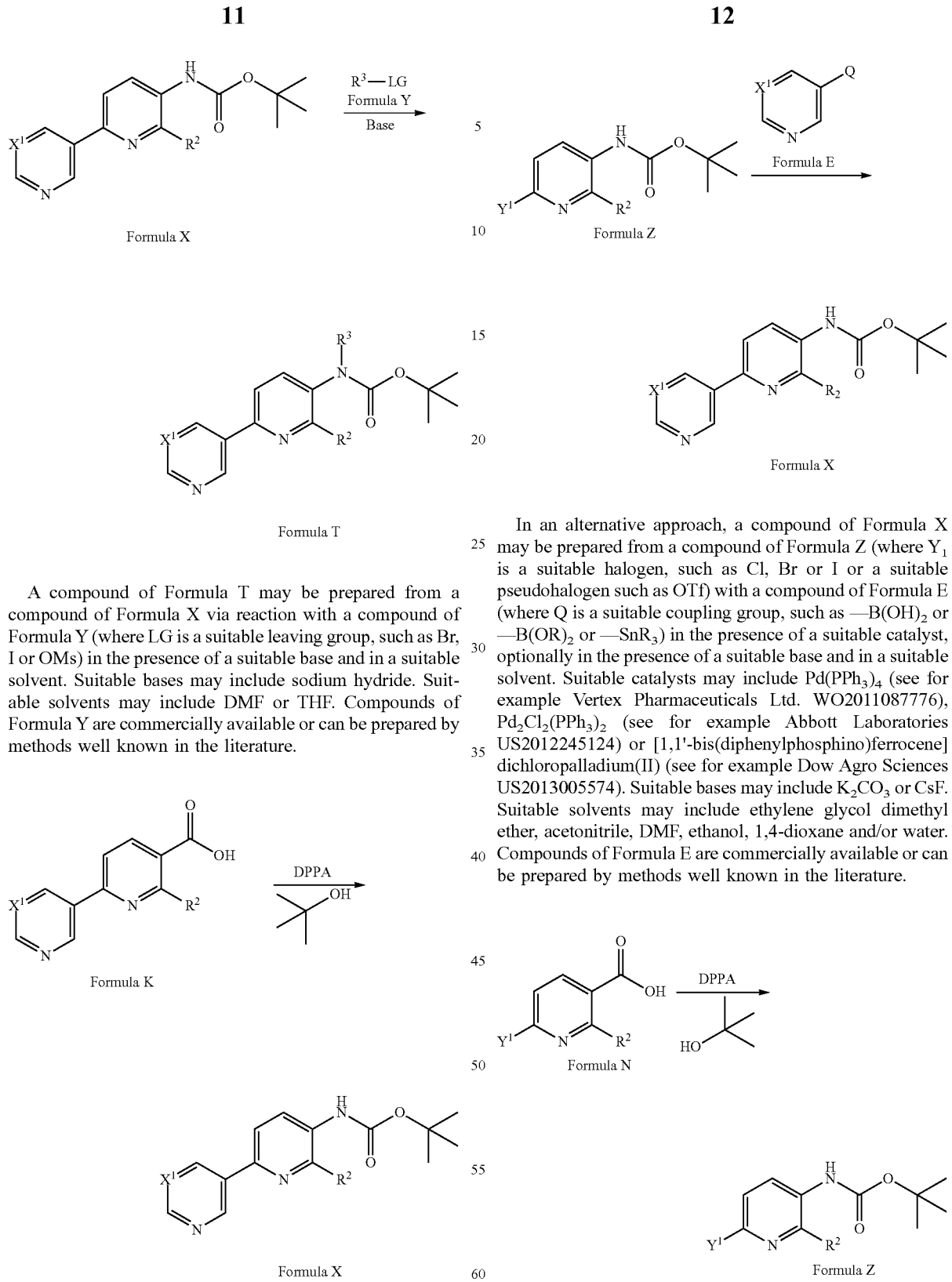

A compound of Formula T may be prepared from a compound of Formula X via reaction with a compound of Formula Y (where LG is a suitable leaving group, such as Br, I or OMs) in the presence of a suitable base and in a suitable solvent. Suitable bases may include sodium hydride. Suitable solvents may include DMF or THF. Compounds of Formula Y are commercially available or can be prepared by methods well known in the literature.

In an alternative approach, a compound of Formula X may be prepared from a compound of Formula Z (where $Y_1$ is a suitable halogen, such as Cl, Br or I or a suitable pseudohalogen such as OTf) with a compound of Formula E (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example Vertex Pharmaceuticals Ltd. WO2011087776), Pd$_2$Cl$_2$(PPh$_3$)$_2$ (see for example Abbott Laboratories US2012245124) or [1,1'-bis(diphenylphosphino)ferrocene]dichloropalladium(II) (see for example Dow Agro Sciences US2013005574). Suitable bases may include K$_2$CO$_3$ or CsF. Suitable solvents may include ethylene glycol dimethyl ether, acetonitrile, DMF, ethanol, 1,4-dioxane and/or water. Compounds of Formula E are commercially available or can be prepared by methods well known in the literature.

A compound of Formula X may be prepared from a compound of Formula K via a Curtius reaction in the presence of a suitable reagent and in the presence of tert-butanol and in a suitable solvent. Suitable reagents may include DPPA. Suitable solvents may include toluene.

A compound of Formula Z may be prepared from a compound of Formula N via a Curtius reaction in the presence of a suitable reagent and in the presence of tert-butanol and in a suitable solvent. Suitable reagents may include DPPA. Suitable solvents may include toluene.

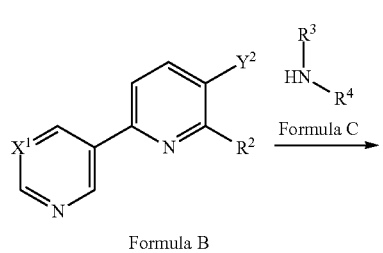

Formula B

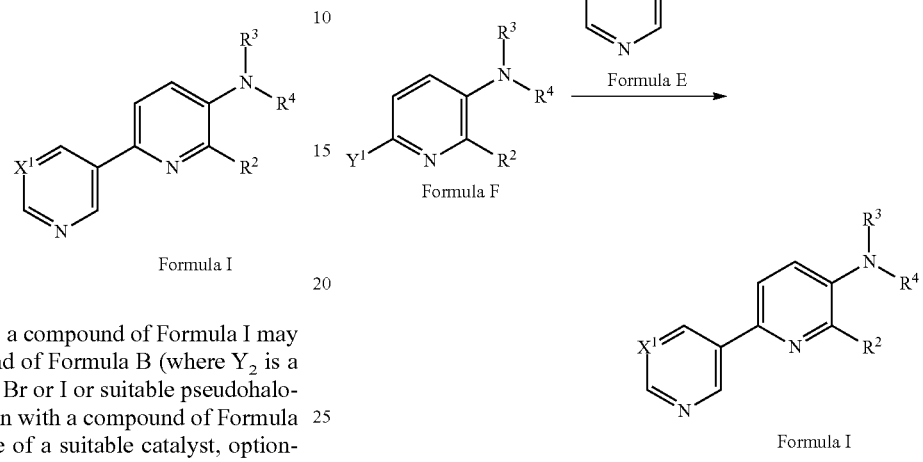

In an alternative approach, a compound of Formula I may be prepared from a compound of Formula B (where $Y_2$ is a suitable halogen, such as Cl, Br or I or suitable pseudohalogen, such as OTf) via reaction with a compound of Formula C, optionally in the presence of a suitable catalyst, optionally in the presence of a suitable ligand and optionally in the presence of a suitable base and in a suitable solvent. Suitable catalyst/ligand systems include $Pd_2dba_3$/BINAP (see for example Y-Q. Long et a/Org. and Biomol. Chem. (2012) 1239). Suitable bases include $NaO^tBu$. Suitable solvents include toluene or tetrahydrofuran. Compounds of Formula C are commercially available or can be prepared by methods well known in the literature.

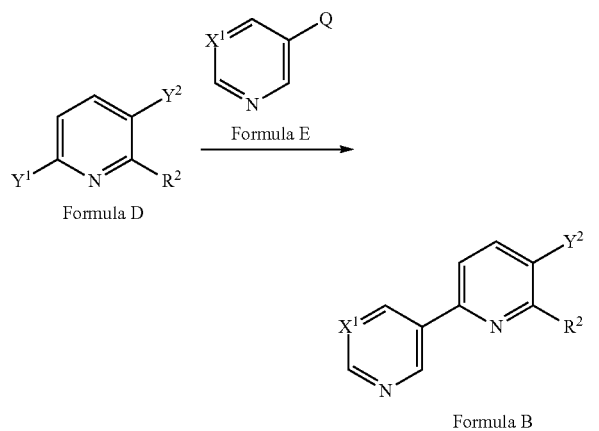

A compound of Formula B may be prepared from a compound of Formula D (where $Y_1$ is a suitable halogen, such as Cl, Br or I or a suitable pseudohalogen, such as OTf) via a cross-coupling reaction with a compound of Formula E (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example Vertex Pharmaceuticals Ltd. WO2011087776), Pd$_2$Cl$_2$(PPh$_3$)$_2$ (see for example Abbott Laboratories US2012245124) or [1,1'-bis(diphenylphosphino)ferrocene]dichloropalladium(II) (see for example Dow Agro Sciences US2013005574). Suitable bases may include $K_2CO_3$ or CsF. Suitable solvents may include ethylene glycol dimethyl ether, acetonitrile, DMF, ethanol, 1,4-dioxane and/or water. Compounds of Formula D and of Formula E are commercially available or can be prepared by methods well known in the literature.

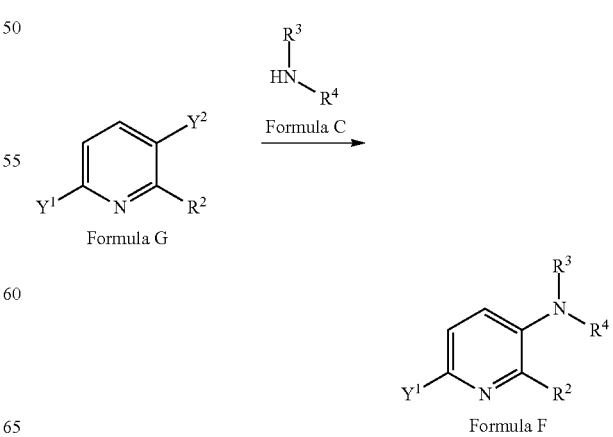

In a further alternative approach, a compound of Formula I may be prepared from a compound of Formula F (where $Y_1$ is a suitable halogen, such as Cl, Br or I or a suitable pseudohalogen, such as OTf) via a cross-coupling reaction with a compound of Formula E (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example Vertex Pharmaceuticals Ltd. WO2011087776 or S. M. Bromidge et al J. Med. Chem. (2000) 1123), Pd$_2$Cl$_2$(PPh$_3$)$_2$ (see for example Abbott Laboratories US2012245124), [1,1'-bis(diphenylphosphino)ferrocene]dichloropalladium(II) (see for example Dow Agro Sciences US2013005574). Suitable bases may include $K_2CO_3$ or CsF. Suitable solvents may include ethylene glycol dimethyl ether, acetonitrile, DMF, ethanol, 1,4-dioxane and/or water. Compounds of Formula E are commercially available or can be prepared by methods well known in the literature.

A compound of Formula F may be prepared from a compound of Formula G (where $Y^2$ is a suitable halogen, such as Br or I or suitable pseudohalogen, such as OTf) via reaction with a compound of Formula C, optionally in the presence of a suitable catalyst and optionally in the presence of a suitable base and in a suitable solvent. Suitable catalyst/ligand systems include $Pd_2dba_3$/BINAP (see for example Y-Q. Long et al Org. and Biomol. Chem. (2012) 1239). Suitable bases include NaO$^t$Bu. Suitable solvents include toluene or tetrahydrofuran Compounds of Formula C and of Formula G are commercially available or can be prepared by methods well known in the literature.

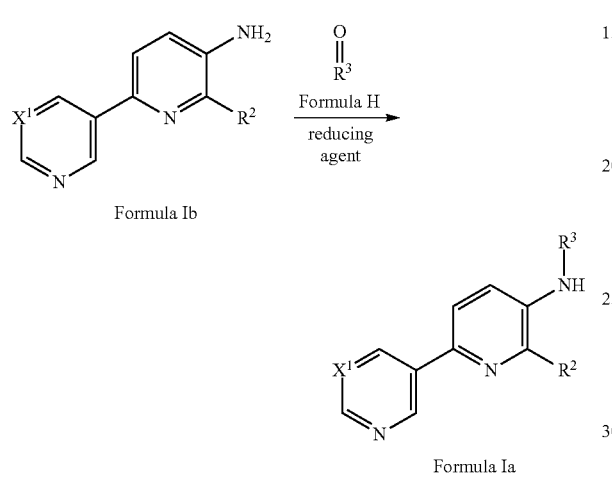

Formula Ib

Formula Ia

A compound of Formula Ia where $R^3$ is not hydrogen may be prepared from a compound of Formula Ib via a reductive amination reaction with a compound of a compound of Formula H in the presence of a suitable reducing agent and in a suitable solvent. Suitable reducing agents include sodium tris(acetoxy)borohydride (see for example C. Kremoser et al Bioorg. Med. Chem. Lett (2010) 4911), sodium borohydride (see for example F. Hoffmann-La Roche WO2007/090752) or sodium cyanoborohydride (see for example S. R. Katamreddy et al J. Med. Chem. (2012), 10972). Suitable solvents include ethanol or methanol. Compounds of Formula H are commercially available or can be prepared by methods well known in the literature.

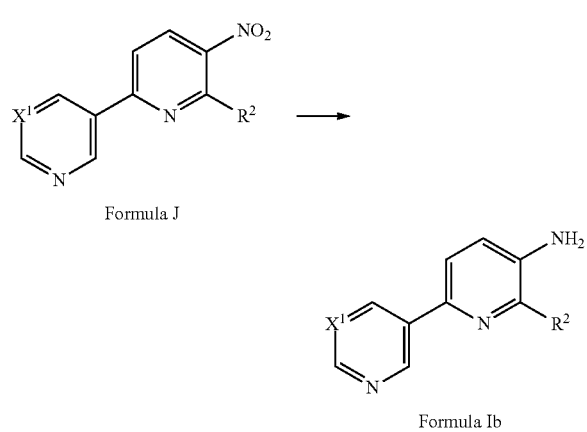

Formula J

Formula Ib

A compound of Formula Ib may be prepared from a compound of Formula J via a reduction reaction optionally in the presence of a suitable catalyst and/or using a suitable reducing agent in a suitable solvent. Suitable catalysts include palladium on charcoal (see for example Z. Gao et al Bioorg. Med. Chem. Lett. (2013) 6269), Raney nickel (see for example Millenium Pharmaceuticals Ltd WO2010/065134). Suitable reducing agents include hydrogen gas, Fe/HCl (see for example A. Gangee et al J. Med. Chem. (1998) 4533), $SnCl_2$ (see for example Pharmacia and Upjohn Company WO2004/099201). Suitable solvents include ethanol, methanol, ethyl acetate or water.

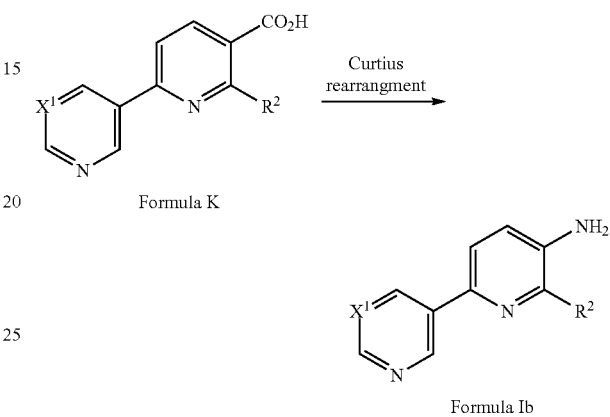

Formula K

Formula Ib

In an alternative approach, a compound of Formula Ib may be prepared from a compound of Formula K via a Curtius rearrangement using a suitable reagent in a suitable solvent. Suitable reagents include DPPA (see for example Takeda Pharmaceutical Company Ltd WO2008/156757) and suitable solvents include DMF or toluene.

Formula L

Formula E

Formula J

A compound of Formula J may be prepared from a compound of Formula L (where $Y^1$ is a suitable halogen, such as Cl, Br or I or suitable pseudohalogen, such as OTf) via a cross-coupling reaction with a compound of Formula E (where Q is a suitable coupling group, such as —B(OH)$_2$ or —B(OR)$_2$ or —SnR$_3$) in the presence of a suitable catalyst, optionally in the presence of a suitable base and in a suitable solvent. Suitable catalysts may include Pd(PPh$_3$)$_4$ (see for example A. P. Johnson et al, ACS Med. Chem. Lett. (2011) 729) or [1,1'-bis(diphenylphosphino)ferrocene]dichloropalladium(II) (see for example Laboratorios Almirall, WO2009021696). Suitable bases may include $K_2CO_3$, Na₂CO₃, Cs₂CO₃, K₃PO₄ or CsF. Suitable solvents may include ethylene glycol dimethyl ether, acetonitrile, DMF, ethanol, 1,4-dioxane, tetrahydrofuran and/or water. Compounds of Formula L and of Formula E are commercially available or can be prepared by methods well known in the literature.

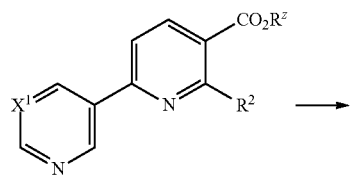

Formula M

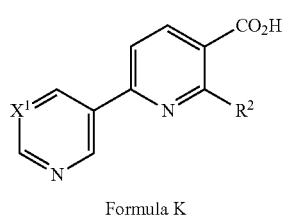

Formula K

A compound of Formula K may be prepared from a compound of Formula M (where $R^z$=$C_{1-6}$ alkyl) via a hydrolysis reaction in the presence of a suitable reagent in a suitable solvent. Suitable reagents include NaOH (see for example F. Giordanetto et al Bioorg. Med. Chem. Lett (2014), 2963), LiOH (see for example AstraZeneca AB, WO2006/073361) or KOH (see for example Kowa Co. Ltd EP1627875). Suitable solvents include H₂O, THF, MeOH or EtOH or mixtures thereof.

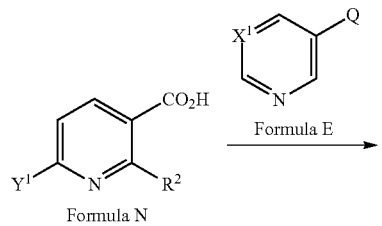

In an alternative approach, a compound of Formula K may be prepared from a compound of Formula N (where $Y^1$ is a suitable halogen, such as Cl, Br or I or suitable pseudohalogen, such as OTf) via a cross-coupling reaction with a compound of Formula E (where Q is a suitable coupling group, such as —B(OH)₂ or —B(OR)₂ or —SnR₃) in the presence of a suitable catalyst, optionally in the presence of a suitable base and in a suitable solvent. Suitable catalysts may include Pd(PPh₃)₄ (see for example Pfizer Limited WO2009/153720) or [1,1'-bis(diphenylphosphino)ferrocene]dichloropalladium(II) (see for example AstraZeneca AB, WO2009/075160). Suitable bases may include K₂CO₃, Na₂CO₃, Cs₂CO₃, K₃PO₄ or CsF. Suitable solvents may include ethylene glycol dimethyl ether, acetonitrile, DMF, ethanol, 1,4-dioxane, tetrahydrofuran and/or water. Compounds of Formula E are commercially available or can be prepared by methods well known in the literature.

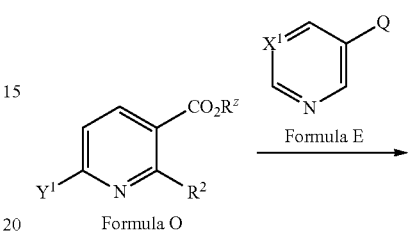

A compound of Formula M may be prepared from a compound of Formula O where $Y_1$ is a suitable halogen (such as Cl, Br or I) or suitable pseudohalogen (such as OTf) via a cross-coupling reaction with a compound of Formula E (where Q is a suitable coupling group, such as —B(OH)₂ or —B(OR)₂ or —SnR₃) in the presence of a suitable catalyst, optionally in the presence of a suitable base and in a suitable solvent. Suitable catalysts may include Pd(PPh₃)₄ (see for example Pfizer Limited WO2009/153720) or [1,1'-bis(diphenylphosphino)ferrocene]dichloropalladium(II) (see for example Cytokinetics Incorporated WO2008/016643). Suitable bases may include K₂CO₃, Na₂CO₃, Cs₂CO₃, K₃PO₄ or CsF. Suitable solvents may include ethylene glycol dimethyl ether, acetonitrile, DMF, ethanol, 1,4-dioxane, tetrahydrofuran and/or water. Compounds of Formula E are commercially available or can be prepared by methods well known in the literature.

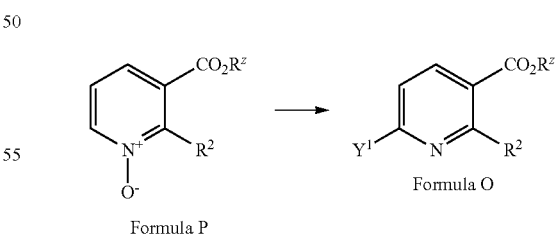

A compound of Formula O (where $Y^1$=a suitable halogen, such as Br or Cl) may be prepared from a compound of Formula P via a halogenation reaction using a suitable reagent, optionally in a suitable solvent. Suitable reagents may include POCl₃ (see for example Takeda Pharmaceutical Co. Ltd. US2011/152273). Suitable solvents may include DCM or DCE.

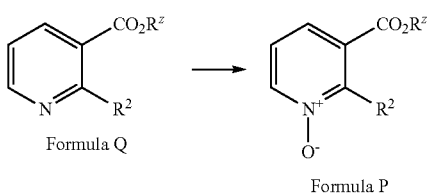

Formula Q → Formula P

A compound of Formula P may be prepared from a compound of Formula Q via an oxidation reaction using a suitable oxidising reagent in a suitable solvent. Suitable oxidants may include 3-chloroperbenzoic acid (see for example Trius Therapeutics Inc. US2012/023875) or urea hydrogen peroxide complex/trifluoroacetic anhydride (see Takeda Pharmaceutical Co. Ltd. US2011/152273). Suitable solvents include DCM or acetonitrile Compounds of Formula Q are commercially available or can be prepared by methods well known in the literature.

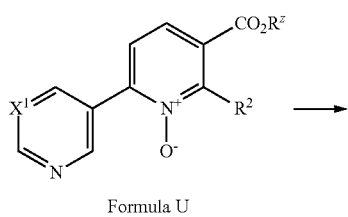

Formula U

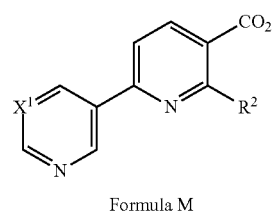

Formula M

In a yet further alternative approach, a compound of Formula M may be prepared from a compound of Formula U via a reduction using a suitable reducing agent optionally in a suitable solvent. Suitable reducing agents include indium/ammonium chloride (see for example J. S. Yadav et al Tet. Lett (2000), 2663) or zinc/ammonium chloride. Suitable solvents may include MeOH, THF or water or combinations thereof.

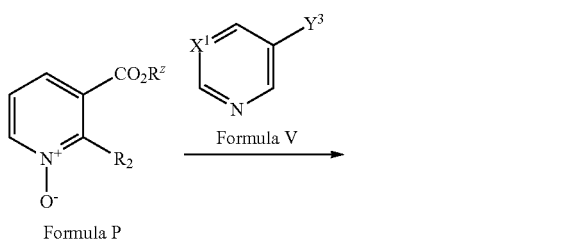

Formula P

Formula U

A compound of Formula U made be prepared from a compound of Formula P via a cross-coupling reaction with a compound of Formula V (where $Y^3$ is a suitable halogen, such as Cl, Br or I or suitable pseudohalogen, such as OTf) in the presence of a suitable catalyst, optionally in the presence of a suitable base and in a suitable solvent. Suitable catalysts include $Pd(OAc)_2$/tri(tert-butyl)phosphonium tetrafluoroboronate (see for example F. Glorius et al JACS (2013) 12204). A suitable base is $K_2CO_3$. A suitable solvent is toluene. Compounds of Formula V are commercially available or can be prepared by methods well known in the literature.

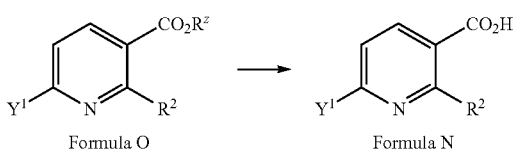

Formula O → Formula N

A compound of Formula N may be prepared from a compound of Formula O where $R^z$ is $C_{1-6}$ alkyl via an ester hydrolysis reaction in the presence of a suitable reagent in a suitable solvent. Suitable reagents may include NaOH (see for example R. Skerlj et al Bioorg. Med. Chem. Lett. (2011), 6950), LiOH (see for example Glaxo Group Ltd. WO2005/075464) or tetra(n-butyl) ammonium hydroxide (see for example Neurogen Corporation WO2004/043925). Suitable solvents may include $H_2O$, THF, MeOH, EtOH or combinations thereof.

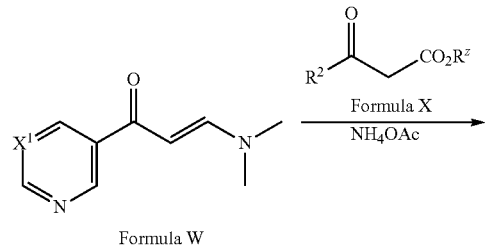

Formula W    Formula X

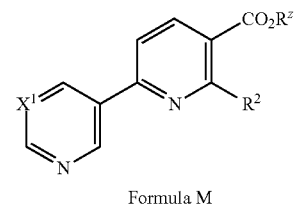

Formula M

In a yet further alternative approach, compounds of Formula M may be prepared from compounds of Formula W by reaction with compounds of Formula X in the presence of ammonium acetate (see for example F. Hoffmann-La Roche WO2008/034579). Compounds of Formula X are commercially available or can be prepared by methods well known in the literature.

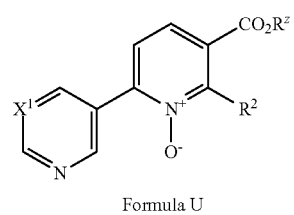

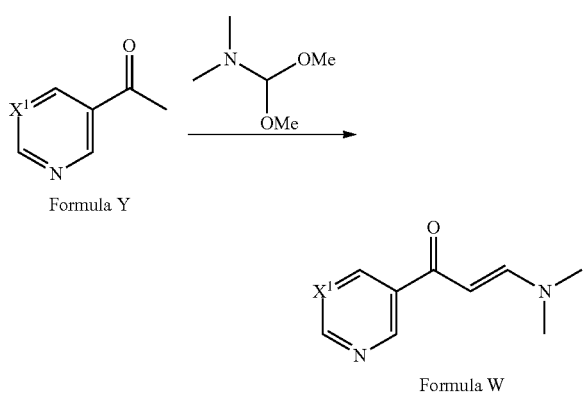

Formula Y

Formula W

Compounds of Formula W may be prepared from compounds of Formula Y by reaction with dimethyl formamide dimethylacetal (see for example F. Hoffmann-La Roche WO2008/034579). Compounds of Formula Y are commercially available or can be prepared by methods well known in the literature.

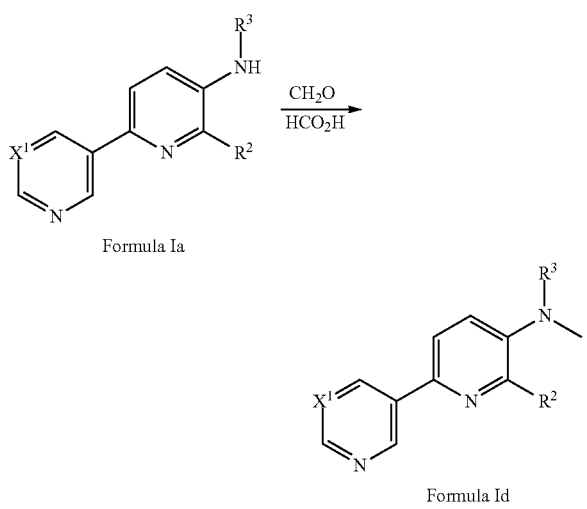

Formula Ia

Formula Id

In a yet further alternative approach, compounds of Formula Id (compounds of Formula I where $R^4$=$CH_3$) may be prepared from compounds of Formula Ia (compounds of Formula I where $R^4$=H) by reaction with formaldehyde in the presence of formic acid, also known as the Eschweiler-Clarke reaction (see for example M. R. Ranga Prabath et al Angew. Chem. Int. Ed. (2015), 8060).

The compounds of Formula (I) as described herein may be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound as described herein and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

Such herbicidal compositions generally comprise from 0.1 to 99% by weight, especially from 0.1 to 95% by weight of compounds of Formula (I) and from 1 to 99.9% by weight of a formulation adjuvant, which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metal s salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

Herbicidal compositions as described herein may further comprise at least one additional pesticide. For example, the compounds of formula (I) can also be used in combination with other herbicides or plant growth regulators. In a preferred embodiment the additional pesticide is a herbicide or herbicide safener. Examples of such mixtures are, in which 'I' represents a compound of Formula (I), I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of formula (I) and/or compositions of the present invention may also be combined with herbicidal compounds disclosed in WO06/024820 and/or WO007/096576.

The mixing partners of the compound of Formula (I) may also be in the form of esters or salts, as mentioned e.g. in The Pesticide Manual, Sixteenth Edition, British Crop Protection Council, 2012.

The compound of Formula (I) can also be used in mixtures with other agrochemicals such as fungicides, nematicides or insecticides, examples of which are given in The Pesticide Manual (supra).

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) as described herein can also be used in combination with one or more safeners. Likewise, mixtures of a compound of Formula (I) as described herein with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula (I) may also be in the form of esters or salts, as mentioned e.g. in The Pesticide Manual (supra). The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

As described above, compounds of formula (I) and/or compositions comprising such compounds may be used in methods of controlling unwanted plant growth, and in particular in controlling unwanted plant growth in crops of useful plants. Thus, the present invention further provides a method of selectively controlling weeds at a locus comprising crop plants and weeds, wherein the method comprises application to the locus, of a weed-controlling amount of a compound of formula (I), or a composition as described herein. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, as well as those where the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous (e.g. grassy) species, for example: *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*; and dicotyledonous species, for example: *Abutilon, Amaranthus, Ambrosia, Chenopodium, Chrysanthemum, Conyza, Galium, Ipomoea, Kochia, Nasturtium, Polygonum, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Preferably the weeds to be controlled and/or growth-inhibited, include monocotyledonous weeds, more preferably grassy monocotyledonous weeds, in particular those from the following genus: *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum*, *Panicum dichotomiflorum* (PANDI), *Panicum miliaceum* (English name "wild proso millet"), *Phalaris minor*, *Phalaris paradoxa*, *Poa annua* (POAAN, English name "annual bluegrass"), *Scirpus maritimus*, *Scirpusjuncoides*, *Setaria viridis* (SETVI, English name "green foxtail"), *Setaria faberi* (SETFA, English name "giant foxtail"), *Setaria glauca*, *Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one embodiment, grassy monocotyledonous weeds to be controlled comprise weeds from the genus: *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria*, and/or *Sorghum*, and/or volunteer corn (volunteer maize) weeds.

In a further embodiment, the grassy monocotyledonous weeds are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment the grassy monocotyledonous weeds, are "cool-season" (cool climate) grassy weeds; in which case they typically comprise weeds from the genus *Agrostis, Alopecurus, Apera, Avena, Bromus, Lolium* and/or *Poa*.

Various aspects and embodiments of the present invention will now be illustrated in more detail by way of example. It will be appreciated that modification of detail may be made without departing from the scope of the invention.

PREPARATION EXAMPLES

[Pd(IPr*)(cin)Cl] refers to the catalyst below—see *Chem. Eur. J.* 2012, 18, 4517

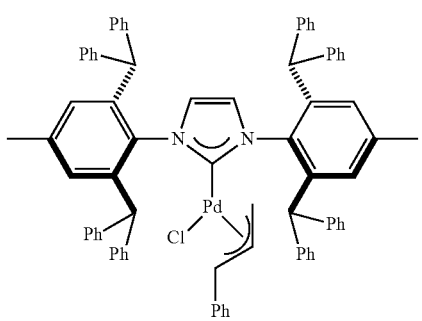

[Pd(IPr*)(cin)Cl]

Xantphos palladacycle 4th generation refers to the catalyst below—see *Org. Lett.* 2014, 16, 4296 and WO13184198.

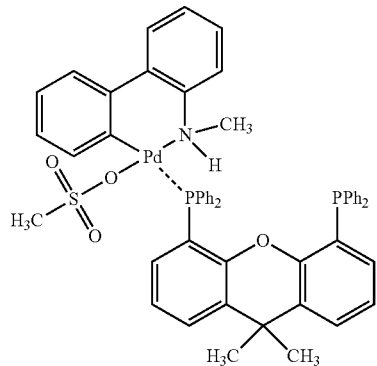

Xantphos palladacycle 3rd generation refers to the catalyst below—see *Chem. Sci.* 2014, 5, 2383 and WO13184198.

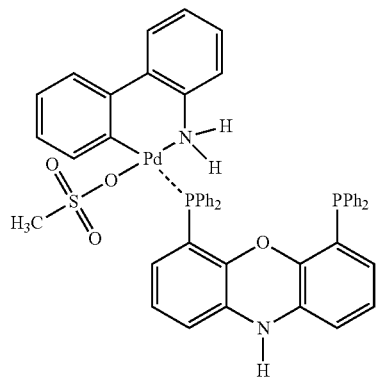

RuPhos palladacycle first generation refers to the catalyst below—*J. Am. Chem. Soc.* 2008, 130, 6686.

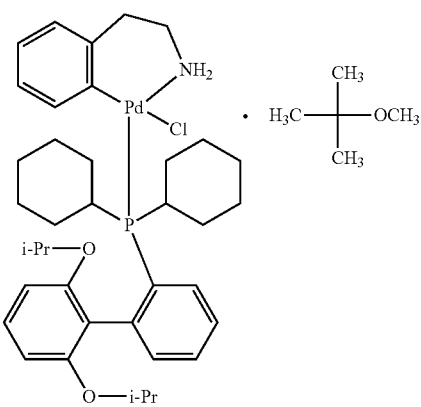

Example P1 Synthesis of 6-(5-fluoro-3-pyridyl)-2-(trifluoromethyl)pyridin-3-amine (Compound A33)

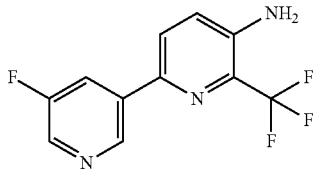 [SMILES: Nc1ccc(-c2cncc(F)c2)nc1C(F)(F)F]

Step 1: Synthesis of ethyl 1-oxido-2-(trifluoromethyl)pyridin-1-ium-3-carboxylate

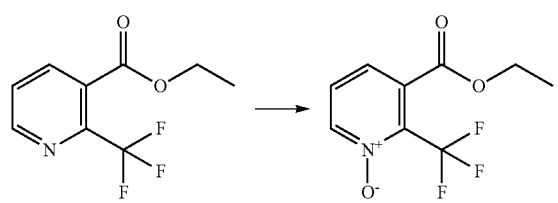 [SMILES: CCOC(=O)c1cccnc1C(F)(F)F ; CCOC(=O)c1ccc[n+]([O-])c1C(F)(F)F]

To a stirred suspension of freshly ground urea hydrogen peroxide addition compound (0.099 g, 1.05 mmol) in DCM (10 mL) at 0° C. was added ethyl 2-(trifluoromethyl)pyridine-3-carboxylate (0.1 g, 0.46 mmol) followed by slow addition (ca. 5 minutes) of a solution of trifluoroacetic anhydride (0.13 mL, 0.91 mmol) in DCM (5 mL). The reaction was allowed to warm to ambient and left stirring overnight. The reaction was washed with 2M aq. sodium carbonate solution (5 mL) and 2M aq sodium metabisulphite solution (2×10 mL) and the solvent was removed in vacuo. The crude product was purified via flash column chromatography on silica gel using an EtOAc/isohexane gradient as eluent to give the desired product (76 mg, 73%) as a thick colourless oil.

$^1$H NMR (400 MHz, CDCl$_3$) δ 8.28 (1H, d), 7.44 (1H, dd), 7.21 (1H, d), 4.43 (2H, q), 1.44 (3H, t)

Step 2: Synthesis of ethyl 6-chloro-2-(trifluoromethyl)pyridine-3-carboxylate

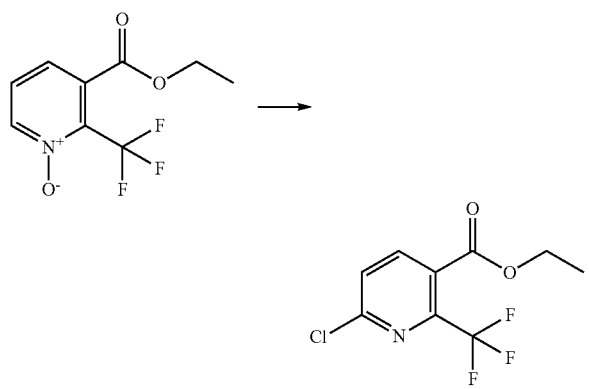

A mixture of ethyl 1-oxido-2-(trifluoromethyl)pyridin-1-ium-3-carboxylate (0.2 g, 0.85 mmol) and POCl$_3$ (2 mL, 21.24 mmol) was heated to 80° C. for 6 hours and then cooled to ambient. The reaction was quenched with 2M aq Na$_2$CO$_3$ solution and then extracted with Et$_2$O (3×15 mL). The combined organic extracts were dried over Na$_2$SO$_4$ and pre-absorbed onto silica for purification via flash column chromatography on silica using an EtOAc/isohexane gradient as eluent to give the desired product (0.14 g, 61%) as a colourless oil.

$^1$H NMR (400 MHz, CDCl$_3$) (8.09 (d, 1H), 7.60 (d, 1H), 4.43 (q, 2H), 1.43 (t, 3H).

Step 3: Synthesis of 6-chloro-2-(trifluoromethyl)pyridine-3-carboxylic acid

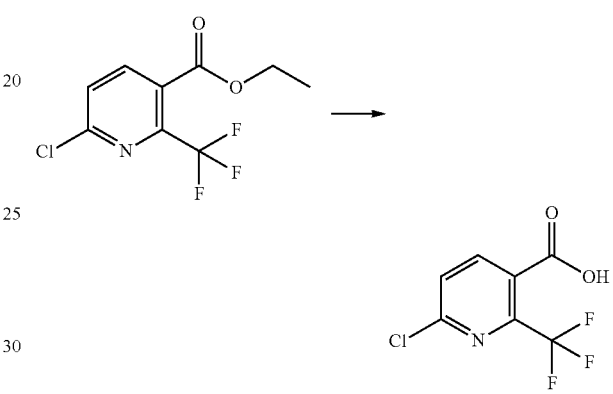

To a solution of ethyl 6-chloro-2-(trifluoromethyl)pyridine-3-carboxylate (190 mg, 0.75 mmol) in THF (4 mL) and H$_2$O (2 mL) was added LiOH.H$_2$O (72 mg, 1.72 mmol) and the reaction stirred at room temperature for 3 h. The reaction was concentrated under reduced pressure and 2N HCl was added slowly to reach pH 3-4, then extracted with EtOAc (2×10 mL). The combined organic extracts were dried over MgSO$_4$ and concentrated to dryness under reduced pressure to give the desired product (170 mg, quant) as a white solid.

$^1$H NMR (400 MHz, CDCl$_3$) δ 8.12 (1H, d), 7.62 (1H, d)

Step 4: Synthesis of tert-butyl N-[6-chloro-2-(trifluoromethyl)-3-pyridyl]carbamate

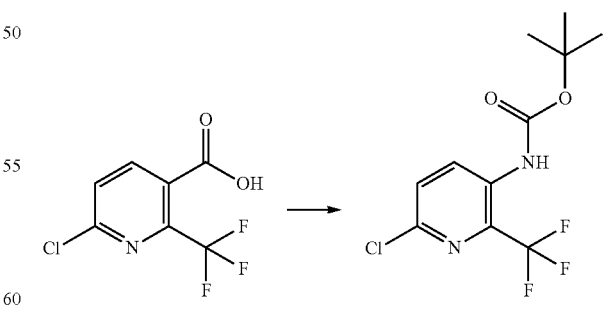

To a stirred solution of 6-chloro-2-(trifluoromethyl)pyridine-3-carboxylic acid (3.0 g, 13.3 mmol) in t-butanol (25 mL) was added triethylamine (17.29 mmol) and diphenylphosphoryl azide (DPPA) (17.29 mmol). This reaction was heated at 90° C. for 2 hrs and then was allowed to cool to room temperature overnight. The reaction mixture was diluted with EtOAc and washed with water (×2), then brine (×1), dried over MgSO₄ and evaporated to dryness under reduced pressure. The crude product was adsorbed onto silica and purified by flash chromatography on silica using a gradient from 5-50% EtOAc/isohexane as eluent to give the desired product (3.24 g, 82%) as a colourless oil.

¹H NMR (400 MHz, CDCl₃) δ 8.64 (d, 1H), 7.48 (d, 1H), 6.89 (br,s 1H), 1.52 (s, 9H)

Step 5: Synthesis of tert-butyl N-[6-(5-fluoro-3-pyridyl)-2-(trifluoromethyl)-3-pyridyl]carbamate

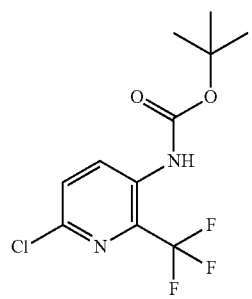

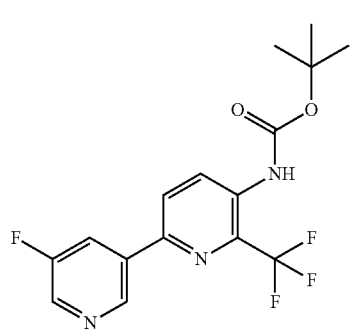

To a stirred suspension of (5-fluoro-3-pyridyl)boronic acid (1.7 g, 1 mmol), Xantphos palladacycle 4th generation (0.2 g, 0.21 mmol) and tert-butyl N-[6-chloro-2-(trifluoromethyl)-3-pyridyl]carbamate (2.50 g, 8.4 mmol) in a mixture of ethanol (6.8 mL) and toluene (25 mL) was added K₂CO₃ (8.4 mL of 2M in water, 17 mmol). The reaction mixture was heated at reflux for 3 hrs. The reaction mixture was cooled to room temperature and concentrated to dryness.

The residue was adsorbed onto silica and purified by flash chromatography on silica using a gradient from 5-100% EtOAc/isohexane as eluent to give the desired compound (2.57 g, 85%).

1H NMR (400 MHz, CDCl₃) δ 9.02 (dd, 1H), 8.79 (d, 1H), 8.52 (d, 1H), 8.12 (m, 1H), 7.94 (d, 1H), 7.01 (br.s, 1H), 1.56 (s, 9H)

Step 6: Synthesis of 6-(5-fluoro-3-pyridyl)-2-(trifluoromethyl)pyridin-3-amine (Compound A33)

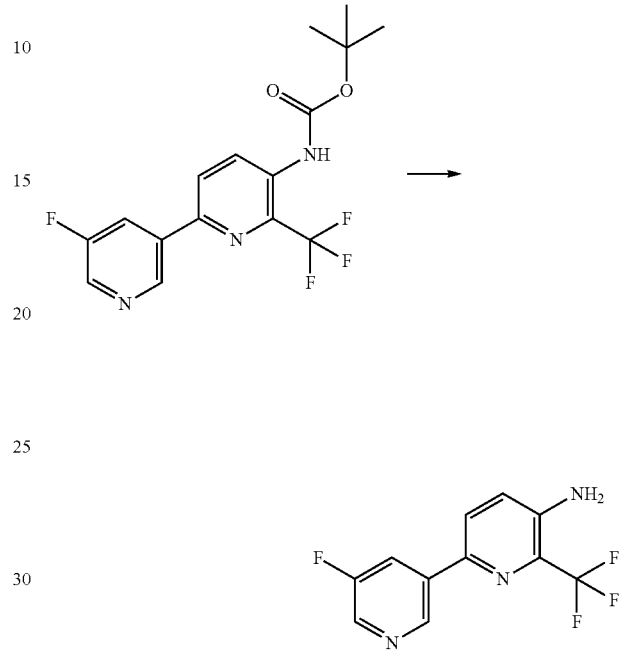

Trifluoroacetic acid (1.4 mL, 18 mmol) was added to tert-butyl N-[6-(5-fluoro-3-pyridyl)-2-(trifluoromethyl)-3-pyridyl]carbamate (685 mg, 1.92 mmol) in DCM (7 mL) and the reaction mixture was heated at reflux for 3 h before being allowed to cool to room temperature. The reaction mixture was partitioned between 2M NaOH (so pH of aqueous was greater than 12) and DCM. The aqueous layer was extracted twice with DCM and the combined organic extracts were dried over MgSO₄ and dry loaded onto celite. Purification by flash chromatography on silica using a gradient of 0-30% EtOAc in isohexane as eluent gave the desired compound (472 mg, 96%) as a white solid.

¹H NMR (400 MHz, CDCl₃) δ 8.93 (m, 1H), 8.45 (d, 1H), 8.12-8.00 (m, 1H), 7.75 (d 1H), 7.21 (d, 1H), 4.38 (br.s, 2H)

Example P2: Synthesis of 6-pyrimidin-5-yl-2-(trifluoromethyl)pyridin-3-amine (Compound A35)

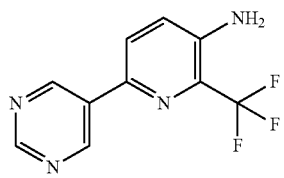 [SMILES: Nc1ccc(-c2cncnc2)nc1C(F)(F)F]

Step 1: Synthesis of tert-butyl N-[6-pyrimidin-5-yl-2-(trifluoromethyl)-3-pyridyl]carbamate

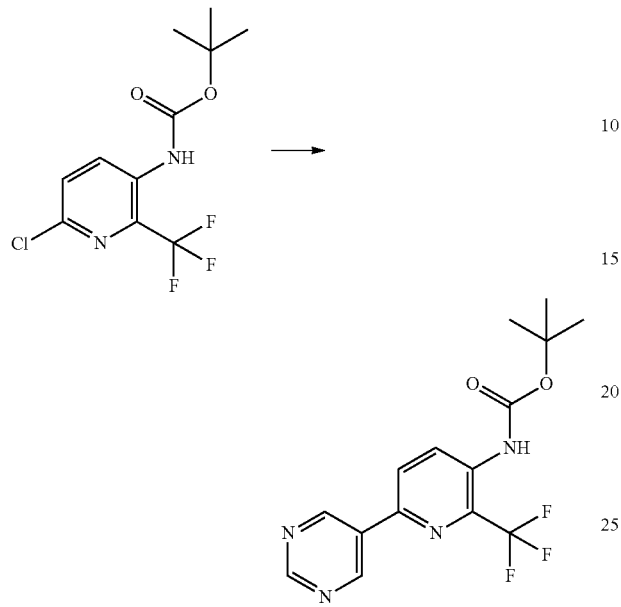

To a stirred suspension of tert-butyl N-[6-chloro-2-(trifluoromethyl)-3-pyridyl]carbamate (2.0 g, 6.74 mmol), pyrimidin-5-ylboronic acid (1.25 g, 10.1 mmol) and [Pd(IPr*)(cin)Cl] (0.395 g, 0.34 mmol) in ethanol (50 mL) was added K₂CO₃ (2.07 g, 14.8 mmol). This mixture was then heated at reflux for 2 hrs. The reaction mixture was adsorbed directly onto silica and purified by flash chromatography on silica using a gradient from 5-100% EtOAc/isohexane as eluent to give the desired product (1.98 g, 86%) as a pale yellow solid.

¹H NMR (400 MHz, CDCl₃) δ 9.33 (s, 2H), 9.27 (s, 1H), 8.81 (d, 1H), 7.92 (d, 1H), 7.02 (br.s, 1H), 1.54 (s, 9H)

Step 2: Synthesis of 6-pyrimidin-5-yl-2-(trifluoromethyl)pyridin-3-amine (Compound A35)

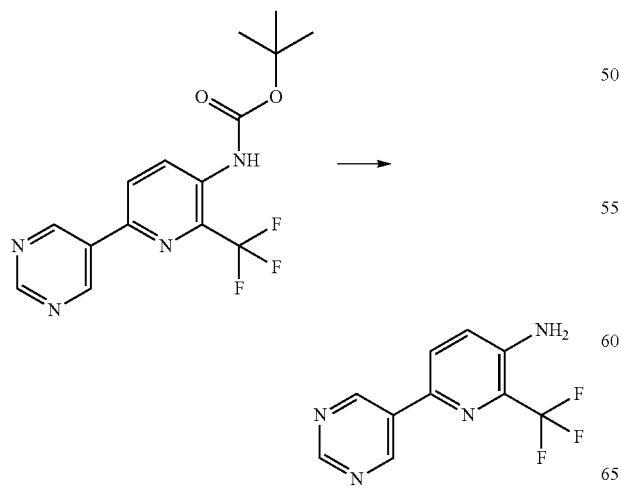

To a solution of tert-butyl N-[6-pyrimidin-5-yl-2-(trifluoromethyl)-3-pyridyl]carbamate (750 mg, 2.20 mmol) in DCM (20 mL) was added, portionwise, TFA (1.70 mL, 22.04 mmol). The reaction mixture was stirred overnight. Saturated sodium bicarbonate solution was added, portionwise, until effervescence ceased. The two layers were separated and the aqueous extracted again with DCM (×2). The organics were combined, washed with brine, dried over MgSO₄ and concentrated to give a yellow solid. The crude product was adsorbed onto silica and purified by flash chromatography on silica using a gradient from 0-10% MeOH in DCM as eluent to give the desired product (404 mg, 76%) as a pale yellow solid.

¹H NMR (400 MHz, CDCl₃) δ 9.28 (s, 2H), 9.21 (s, 1H), 7.74 (d, 1H), 7.23 (d, 1H), 4.43 (br.s, 2H)

Example P3 Synthesis of 6-(5-fluoro-3-pyridyl)-N-phenyl-2-(trifluoromethyl)pyridin-3-amine (Compound A32)

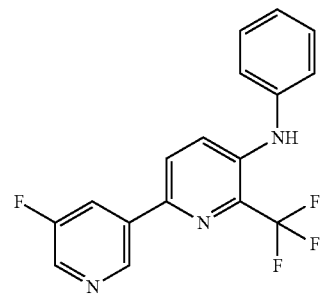 [SMILES: Fc1cncc(-c2ccc(Nc3ccccc3)c(C(F)(F)F)n2)c1]

Step 1: Synthesis of 6-(5-fluoro-3-pyridyl)-N-phenyl-2-(trifluoromethyl)pyridin-3-amine (Compound A32)

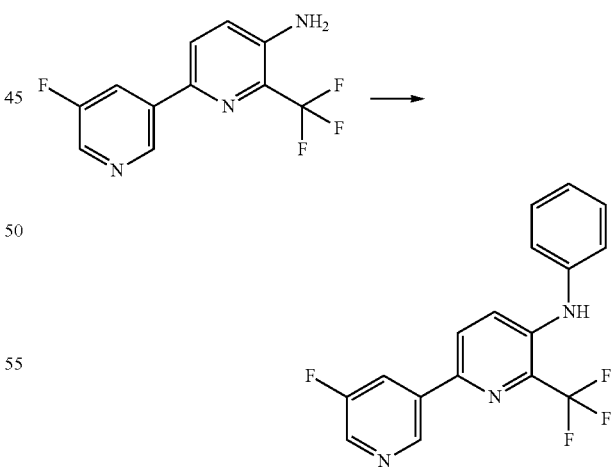

To a microwave vial was added bromobenzene (0.39 mmol, 0.061 g), 6-(5-fluoro-3-pyridyl)-2-(trifluoromethyl)pyridin-3-amine (0.1 g, 0.39 mmol), Xantphos palladacycle 3rd generation (0.031 mmol, 0.033 g), caesium carbonate (0.19 g, 0.58 mmol) and toluene (2 mL). The vial was capped and heated under microwave irradiation for 40 minutes at 130° C. The mixture was filtered, concentrated and purified by flash chromatography on silica using an EtOAc/isohexane gradient as eluent to afford the desired product (18 mg, 14%) as a yellow gum.

$^1$H NMR (400 MHz, CDCl$_3$) δ 8.95 (s, 1H), 8.47 (d, 1H), 8.09 (m, 1H), 7.76 (d, 1H), 7.67 (d, 1H), 7.44-7.36 (m, 2H), 7.22-7.16 (m, 3H), 6.32 (br.s, 1H)

Example P4: Synthesis of 6-(5-fluoro-3-pyridyl)-N-methyl-2-(trifluoromethyl)pyridin-3-amine (Compound A34)

Step 1: Synthesis of tert-butyl N-[6-(5-fluoro-3-pyridyl)-2-(trifluoromethyl)-3-pyridyl]-N-methyl-carbamate A solution of tert-butyl N-[6-pyrimidin-5-yl-2-(trifluoromethyl)-3-pyridyl]carbamate (422 mg, 1.240 mmol) in N,N-dimethylformamide (4.2 mL) was cooled to 5° C. (ice bath), under nitrogen. Sodium hydride (60% dispersion in mineral oil) (1.49 mmol, 0.060 g) was added in one portion. This mixture was allowed to warm to room temperature and stir for 1 hr, then iodomethane (1.86 mmol) was added and the reaction mixture stirred for a further 2 hrs. The reaction mixture was diluted carefully with water and extracted with EtOAc (×3). The organics were combined, washed with brine, dried over MgSO$_4$ and concentrated to give a yellow gum. The crude product was adsorbed directly onto silica and purified by flash chromatography on silica using a gradient from 5-100% EtOAc in isohexane as eluent to give the desired product (354 mg, 81%) as an orange gum.

$^1$H NMR (400 MHz, CDCl$_3$, major rotamer) δ 9.07 (s, 1H), 8.57 (d, 1H), 8.20 (br.d, 1H), 8.01 (d, 1H), 7.76 (d, 1H), 3.22 (s, 3H), 1.33 (s, 9H)

Step 2: Synthesis of 6-(5-fluoro-3-pyridyl)-N-methyl-2-(trifluoromethyl)pyridin-3-amine (Compound A34)

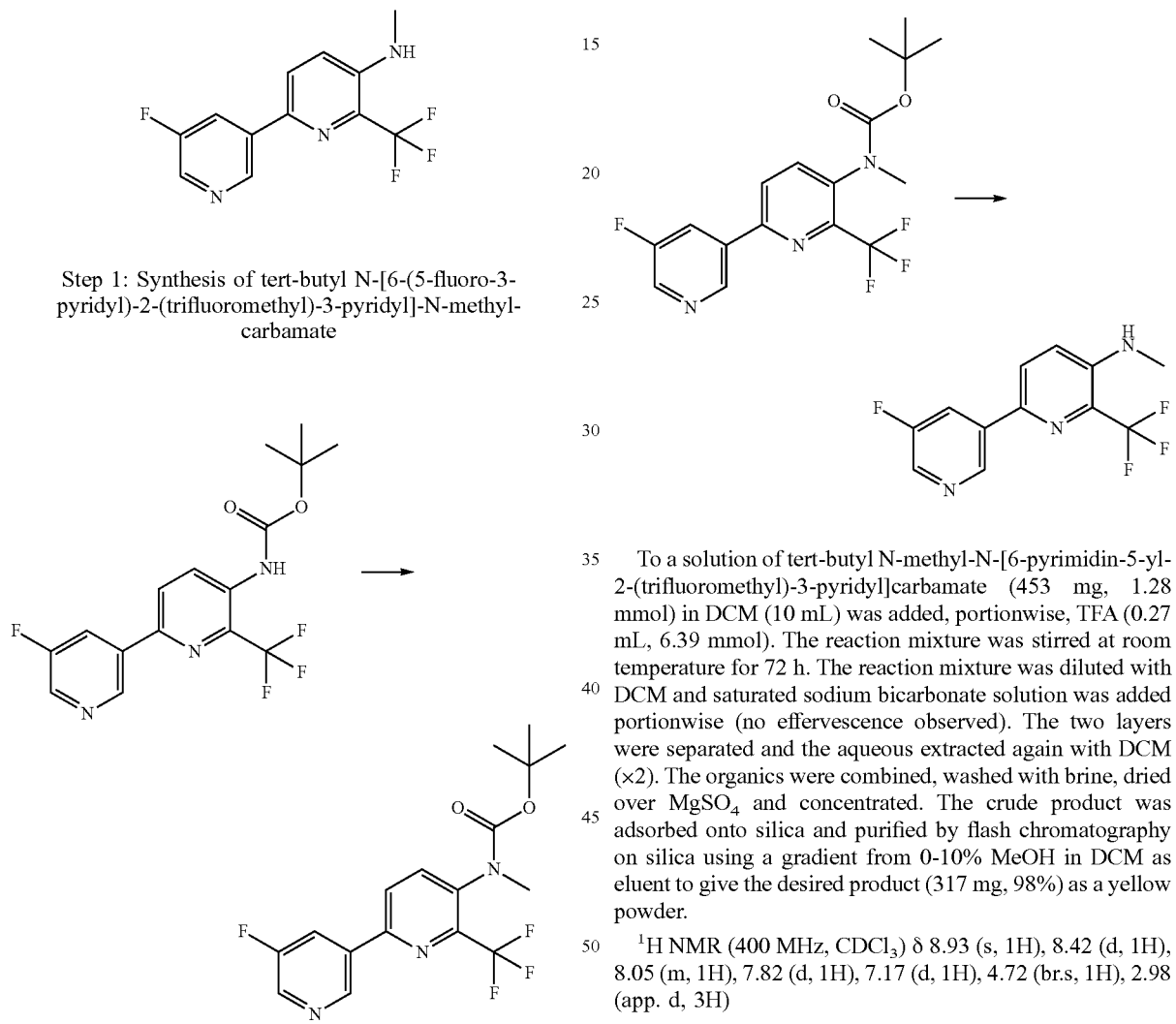

To a solution of tert-butyl N-methyl-N-[6-pyrimidin-5-yl-2-(trifluoromethyl)-3-pyridyl]carbamate (453 mg, 1.28 mmol) in DCM (10 mL) was added, portionwise, TFA (0.27 mL, 6.39 mmol). The reaction mixture was stirred at room temperature for 72 h. The reaction mixture was diluted with DCM and saturated sodium bicarbonate solution was added portionwise (no effervescence observed). The two layers were separated and the aqueous extracted again with DCM (×2). The organics were combined, washed with brine, dried over MgSO$_4$ and concentrated. The crude product was adsorbed onto silica and purified by flash chromatography on silica using a gradient from 0-10% MeOH in DCM as eluent to give the desired product (317 mg, 98%) as a yellow powder.

$^1$H NMR (400 MHz, CDCl$_3$) δ 8.93 (s, 1H), 8.42 (d, 1H), 8.05 (m, 1H), 7.82 (d, 1H), 7.17 (d, 1H), 4.72 (br.s, 1H), 2.98 (app. d, 3H)

Example P5 Synthesis of 3-amino-6-(5-fluoro-3-pyridyl)pyridine-2-carbonitrile (Compound A9)

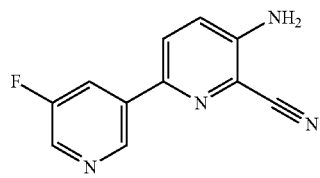 [SMILES: N#Cc1nc(-c2cncc(F)c2)ccc1N]

Step 1: Synthesis of 3-amino-6-(5-fluoro-3-pyridyl)pyridine-2-carbonitrile (Compound A9)

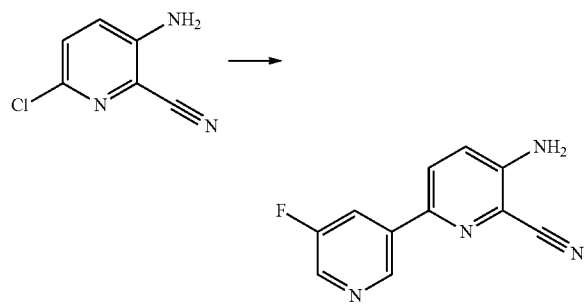

A mixture of 3-amino-6-chloro-pyridine-2-carbonitrile (330 mg, 2.15 mmol), 5-fluoropyridine-3-boronic acid (394 mg, 2.69 mmol), potassium carbonate (633 mg, 4.73 mmol) and [Pd(IPr*)(cin)Cl] (126 mg, 0.11 mmol) in EtOH (9.9 mL) was heated at 80° C. for 1 hour under an $N_2$ atmosphere and then allowed to cool to room temperature. The mixture was filtered through celite and concentrated in vacuo. The resultant orange-brown gum was adsorbed onto silica and purified by flash chromatography on silica using an EtOAc/isohexane gradient as eluent to give the desired product (80 mg, 17%) as a brown gum.

$^1$H NMR (400 MHz, $CD_3OD$) δ 8.95 (d, 1H), 8.43 (d, 1H), 8.18-8.09 (m, 1H), 7.93 (d, 1H), 7.35 (d, 1H)

Example P6 Synthesis of 4-[6-(5-fluoro-3-pyridyl)-2-(trifluoromethyl)-3-pyridyl]morpholine (Compound A39)

A mixture of 3,6-dichloro-2-(trifluoromethyl)pyridine (200 mg, 0.94 mmol) and (5-fluoro-3-pyridyl)boronic acid (144 mg, 1.02 mmol) in ethanol (0.54 mL), toluene (2 mL) and $H_2O$ (0.93 mL) was sparged with $N_2$ for 30 minutes. $K_2CO_3$ (256 mg, 1.85 mmol) and Xantphos palladacycle G4 (22 mg, 0.023 mmol) were added and the reaction heated at 80° C. under an $N_2$ atmosphere for 2 hours. The reaction was allowed to cool to RT, diluted with $H_2O$ (10 mL) and extracted with EtOAc (3×10 mL). The combined organic extracts were dried over $MgSO_4$ and evaporated to dryness under reduced pressure to give a yellow oil. The crude product was purified by flash chromatography on silica gel using an EtOAc/isohexane gradient as eluent to give the desired product (0.192 g, 75%) as a colourless oil that solidified on standing.

$^1$H NMR (400 MHz, $CDCl_3$) δ 9.03 (s, 1H), 8.58 (s, 1H), 8.15 (d, 1H), 7.98 (d, 1H), 7.92 (d, 1H).

Step 2: Synthesis of 4-[6-(5-fluoro-3-pyridyl)-2-(trifluoromethyl)-3-pyridyl]morpholine (Compound A39)

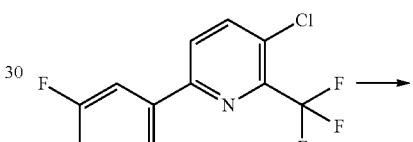

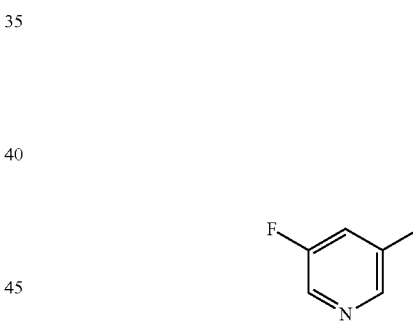

A microwave vial was charged with 3-chloro-6-(5-fluoro-3-pyridyl)-2-(trifluoromethyl)pyridine (150 mg, 0.542 mmol), RuPhos palladacycle first generation (11 mg, 0.014 mmol), RuPhos (7 mg, 0.014 mmol), NaO$^t$Bu (65 mg, 0.65 mmol), morpholine (0.06 mL, 0.65 mmol) and THF (1 mL). The reaction was heated at 120° C. under microwave irradiation for 1 hour and allowed to cool to RT. The reaction was diluted with DCM (20 mL) and washed with water (20 mL). The aqueous phase was extracted with DCM (2×20 mL), the combined organic extracts dried over $MgSO_4$ and evaporated to dryness under reduced pressure. The crude product was purified by flash chromatography on silica gel using an EtOAc/isohexane gradient as eluent to give the desired product (117 mg, 66%) as a pale yellow solid.

$^1$H NMR (400 MHz, $CDCl_3$) δ 9.00 (s, 1H), 8.51 (d, 1H), 8.16-8.11 (m, 1H), 7.93 (d, 1H), 7.74 (d, 1H), 3.92-3.86 (m, 4H), 3.07-3.00 (m, 4H).

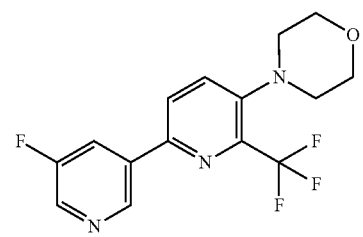 [SMILES: Fc1cncc(-c2ccc(N3CCOCC3)c(C(F)(F)F)n2)c1]

Step 1: Synthesis of 3-chloro-6-(5-fluoro-3-pyridyl)-2-(trifluoromethyl)pyridine

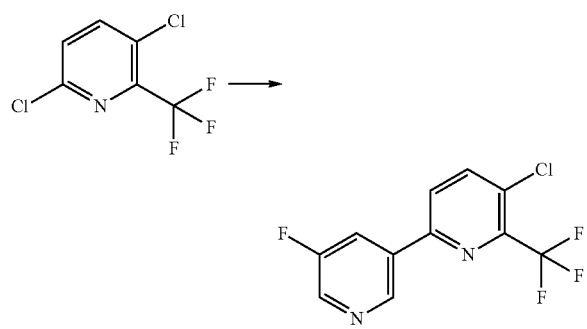

Example P7: Synthesis of N-(cyclobutylmethyl)-6-(5-fluoro-3-pyridyl)-2-(trifluoromethyl)pyridin-3-amine (Compound A51)

Example P8: Synthesis of 6-(5-fluoro-3-pyridyl)-N,N-dimethyl-2-(trifluoromethyl)pyridin-3-amine (compound A38)

Step 1: Synthesis of N-(cyclobutylmethyl)-6-(5-fluoro-3-pyridyl)-2-(trifluoromethyl)pyridin-3-amine (Compound A51)

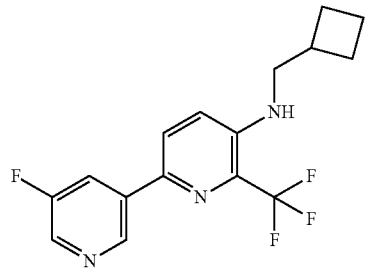 [SMILES: Fc1cncc(-c2ccc(NCC3CCC3)c(C(F)(F)F)n2)c1]

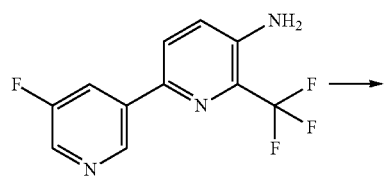

To a stirred solution of 6-(5-fluoro-3-pyridyl)-2-(trifluoromethyl)pyridin-3-amine (130 mg, 0.50 mmol) and cyclobutanaldehyde (73 mg, 0.85 mmol) in EtOAc (1.6 mL) was added trifluoroacetic acid (0.12 mL, 1.5 mmol) followed by portionwise addition of sodium triacetoxyborohydride (210 mg, 0.95 mmol). The reaction was stirred at RT for 2 hours, then quenched with 2N NaOH (3 mL), stirred vigorously for 5 minutes and extracted with EtOAc (3×5 mL). The combined organic extracts were evaporated to dryness under reduced pressure and purified by flash chromatography on silica gel using an EtOAc/isohexane gradient as eluent to give the desired product (102 mg, 63%) as a colourless oil.

$^1$H NMR (400 MHz, CDCl$_3$) δ 8.92 (s, 1H), 8.42 (d, 1H), 8.08-8.01 (m, 1H), 7.78 (d, 1H), 7.16 (d, 1H), 4.54 (br s, 1H), 3.23 (dd, 2H), 2.66 (m, 1H), 2.22-2.10 (m, 2H), 2.04-1.87 (m, 2H), 1.85-1.73 (m, 2H).

Step 1: Synthesis of 6-(5-fluoro-3-pyridyl)-N,N-dimethyl-2-(trifluoromethyl)pyridin-3-amine (compound A38)

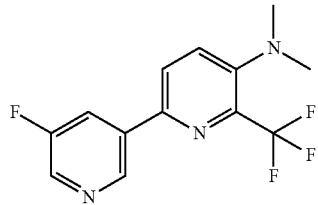 [SMILES: CN(C)c1ccc(-c2cncc(F)c2)nc1C(F)(F)F]

To a stirred solution of 6-(5-fluoro-3-pyridyl)-2-(trifluoromethyl)pyridin-3-amine (300 mg, 1.17 mmol) in formic acid (4.5 mL) at 0° C. was added formaldehyde (37% solution in water) (3.75 mL 50.4 mmol) and the mixture allowed to warm to RT. The reaction was heated at reflux for 20 hours and then allowed to cool to RT. The reaction mixture was diluted in water (40 mL) then made basic by the careful addition of dil. aq. NaOH. The emulsion was then extracted with Et2O (3×50 mL) and the combined organic extracts were dried over MgSO$_4$ and evaporated to dryness under reduced pressure. The crude yellow product was purified by flash chromatography on silica gel using an EtOAc/isohexane gradient as eluent to give the desired product (249 mg, 75%) as a very pale yellow oil which crystallised over time.

$^1$H NMR (400 MHz, CDCl$_3$) δ 8.97 (s, 1H), 8.48 (s, 1H), 8.12 (dt, 1H), 7.85 (d, 1H), 7.61 (d, 1H,), 2.90 (s, 6H).

Further examples of the invention were made in an analogous manner using the methods described above in Examples P1 to P8, with respect to compounds A33, A35, A32, A34, A9, A39, A51 and A38. Table 2 below, shows the structure of these compounds and the physical characterising data obtained using one or more of methods A to C as outlined below.

TABLE 2

Characterising data for Compounds of formula (I) made by the methods described above.

| Cmpd ID | Structure | $^1$H NMR Data (400 MHz, CDCl$_3$ unless stated) | m/z | method |
|---|---|---|---|---|
| A1 | 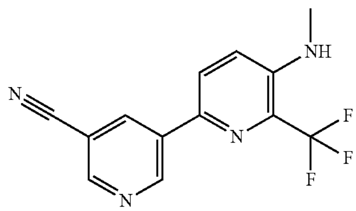 [SMILES: CNc1ccc(-c2cncc(C#N)c2)nc1C(F)(F)F] | 9.31 (s, 1H), 8.81 (s, 1H), 8.58 (s, 1H), 7.83 (d, 1H), 7.19 (d, 1H), 4.80 (br. s, 1H), 2.99 (app. d, 3H) | [MH+] 279; tr 0.64 mins | C |
| A2 | 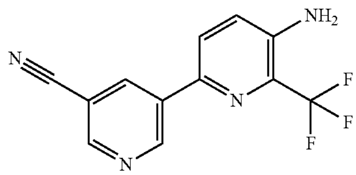 [SMILES: N#Cc1cncc(-c2ccc(N)c(C(F)(F)F)n2)c1] | 9.31 (s, 1H), 8.83 (s, 1H), 8.58 (s, 1H), 7.77 (d, 1H), 7.23 (d, 1H), 4.47 (s, 2H) | — | — |
| A3 | 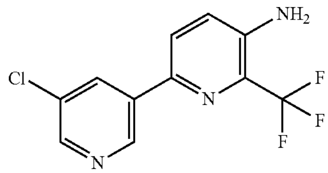 [SMILES: Nc1ccc(-c2cncc(Cl)c2)nc1C(F)(F)F] | 8.99 (s, 1H), 8.54 (s, 1H), 8.31 (s, 1H), 7.72 (d, 1H), 7.21 (d, 1H), 4.39 (br. s, 2H) | — | — |
| A4 | 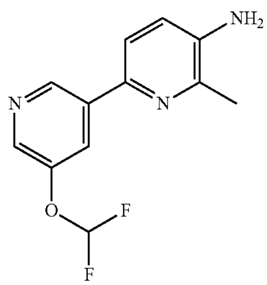 [SMILES: Cc1nc(-c2cncc(OC(F)F)c2)ccc1N] | 8.95 (s, 1H), 8.40 (s, 1H), 8.08 (s, 1H), 7.45 (d, 1H), 7.00 (d, 1H), 6.61 (t, 1H), 3.81 (br. s, 2H), 2.49 (s, 3H) | — | — |
| A5 | 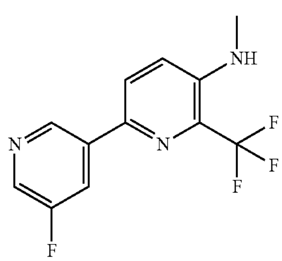 [SMILES: CNc1ccc(-c2cncc(F)c2)nc1C(F)(F)F] | 8.93 (s, 1H), 8.42 (d, 1H), 8.05 (m, 1H), 7.82 (d, 1H), 7.17 (d, 1H), 4.72 (br. s, 1H), 2.98 (app. d, 3H) | [MH+] 272; tr 0.67 mins | C |
| A6 | 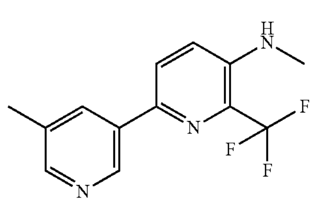 [SMILES: CNc1ccc(-c2cncc(C)c2)nc1C(F)(F)F] | 8.90 (s, 1H), 8.39 (s, 1H), 8.10 (s, 1H), 7.79 (d, 1H), 7.14 (d, 1H), 4.71 (br. s, 1H), 2.94 (app. d, 3H), 2.39 (s, 3H) | [MH+] 268; tr 0.39 mins | C |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A7 | 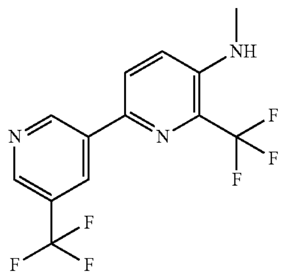 [SMILES: CNc1ccc(-c2cncc(C(F)(F)F)c2)nc1C(F)(F)F] | 9.31 (s, 1H), 8.71 (s, 1H), 8.50 (s, 1H), 7.85 (d, 1H), 7.19 (d, 1H), 4.76 (br. s, 1H), 2.98 (app. d, 3H) | [MH+] 322; tr 0.78 mins | C |
| A8 | 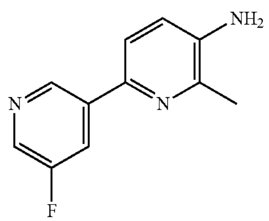 | 8.91 (s, 1H), 8.39 (d, 1H), 8.02 (m, 1H), 7.47 (d, 1H), 7.01 (d, 1H), 3.78 (br. s ,2H), 2.50 (s, 3H) | — | — |
| A9 | 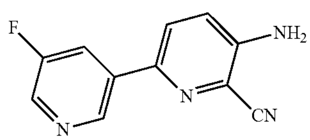 [SMILES: N#Cc1nc(-c2cncc(F)c2)ccc1N] | (CD₃OD) 8.95 (d, 1H), 8.43 (d, 1H), 8.18-8.09 (m, 1H), 7.93 (d, 1H), 7.35 (d, 1H) | — | — |
| A10 | 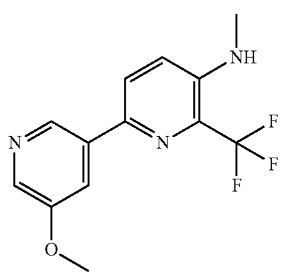 [SMILES: CNc1ccc(-c2cncc(OC)c2)nc1C(F)(F)F] | 8.70 (d, 1H), 8.27 (d, 1H), 7.88-7.84 (m, 1H), 7.81 (d, 1H), 7.17 (d, 1H), 4.67 (br. s, 1H), 3.93 (s, 3H), 2.97 (3H, app. d) | [MH+] 284; tr 0.46 mins | C |
| A11 | 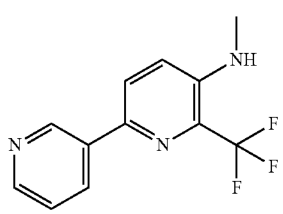 [SMILES: CNc1ccc(-c2cccnc2)nc1C(F)(F)F] | 9.12 (d, 1H), 8.58 (m, 1H), 8.29 (m, 1H), 7.81 (d, 1H), 7.49-7.33 (m, 1H), 7.18 (d, 1H), 4.67 (br. s, 1H), 2.97 (app. d, 3H) | [MH+] 254; tr 0.36 mins | C |
| A12 | 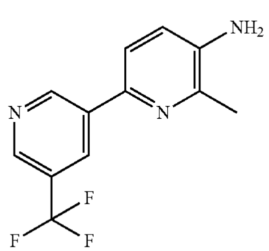 [SMILES: Cc1nc(-c2cncc(C(F)(F)F)c2)ccc1N] | 9.28 (d, 1H), 8.79 (s, 1H), 8.51 (s, 1H), 7.51 (d, 1H), 7.02 (d, 1H), 3.80 (br. s, 2H), 2.51 (s, 3H) | — | — |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A13 | 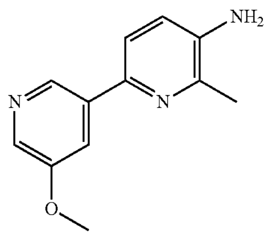 [SMILES: COc1cncc(-c2ccc(N)c(C)n2)c1] | 8.68 (d, 1H), 8.24 (d, 1H), 7.82 (m, 1H), 7.45 (d, 1H), 7.00 (d, 1H), 3.93 (s, 3H), 3.73 (br. s, 2H), 2.50 (s, 3H) | — | — |
| A14 | 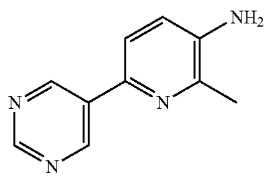 | 9.24 (s, 2H), 9.14 (s, 1H), 7.45 (d, 1H), 7.02 (d, 1H), 3.81 (br. s, 2H), 2.50 (s, 3H) | — | — |
| A15 | 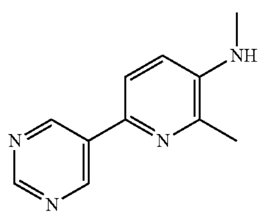 | 9.23 (s, 2H), 9.11 (s, 1H), 7.53 (d, 1H), 6.90 (d, 1H), 3.87 (br. s, 1H), 2.95 (app. d, 3H), 2.47 (s, 3H) | [MH+] 201; tr 0.29 mins | C |
| A16 | 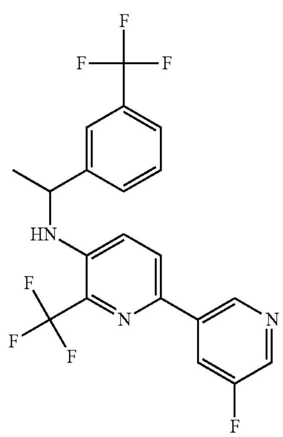 [SMILES: CC(Nc1ccc(-c2cncc(F)c2)nc1C(F)(F)F)c1cccc(C(F)(F)F)c1] | 8.88 (s, 1H), 8.43 (d, 1H), 8.04 (m, 1H), 7.64-7.58 (m, 2H), 7.56-7.47 (m, 3H), 6.82 (d, 1H), 5.01 (br. s, 1H), 4.62 (m, 1H), 1.62 (d, 3H) | [MH+] 430; tr 1.64 mins | A |
| A17 | 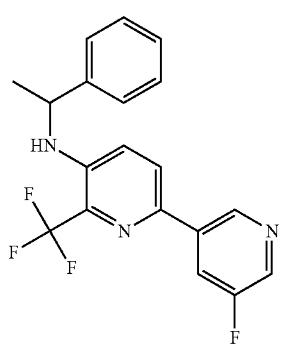 [SMILES: CC(Nc1ccc(-c2cncc(F)c2)nc1C(F)(F)F)c1ccccc1] | 8.88 (s, 1H), 8.42 (d, 1H), 8.06 (m, 1H), 7.58 (d, 1H), 7.38-7.22 (m, 5H), 6.93 (d, 1H), 5.03 (br. s, 1H), 4.56 (m, 1H), 1.62 (d, 3H) | [MH+] 262; tr 1.57 mins | A |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A18 | 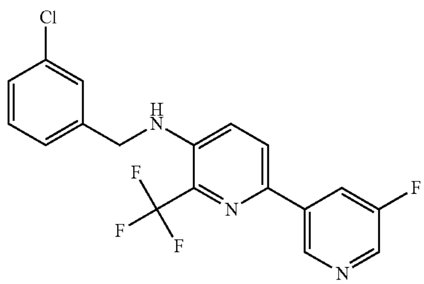 [SMILES: Fc1cncc(-c2ccc(NCc3cccc(Cl)c3)c(C(F)(F)F)n2)c1] | 8.89 (s, 1H), 8.48 (d, 1H), 8.04 (m, 1H), 7.72 (d, 1H), 7.38-7.22 (m, 4H), 7.03 (d, 1H), 5.18 (br. s, 1H), 4.48 (app. d, 2H) | [MH+] 382; tr 1.54 mins | A |
| A19 | 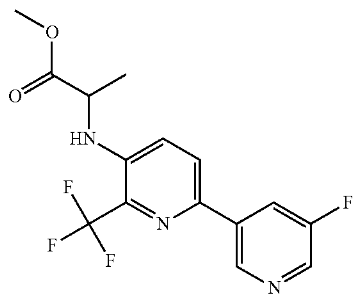 [SMILES: COC(=O)C(C)Nc1ccc(-c2cncc(F)c2)nc1C(F)(F)F] | 8.92 (s, 1H), 8.44 (d, 1H), 8.14-7.98 (m, 1H), 7.79 (d, 1H), 7.09 (d, 1H), 5.16 (br. d, 1H), 4.23 (m, 1H), 3.80 (s, 3H), 1.58 (d, 3H) | — | — |
| A20 | 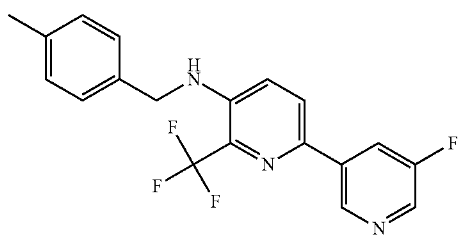 [SMILES: Cc1ccc(CNc2ccc(-c3cncc(F)c3)nc2C(F)(F)F)cc1] | 8.91 (s, 1H), 8.42 (d, 1H), 8.03 (m, 1H), 7.71 (d, 1H), 7.24 (d, 2H), 7.16 (d, 2H), 7.11 (d, 1H), 5.08 (br. s, 1H), 4.41 (app. d, 2H), 2.32 (s, 3H) | [MH+] 362; tr 1.55 mins | A |
| A21 | 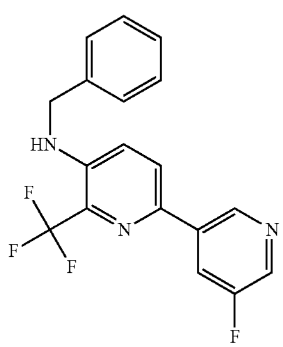 [SMILES: Fc1cncc(-c2ccc(NCc3ccccc3)c(C(F)(F)F)n2)c1] | 8.82 (s, 1H), 8.43 (d, 1H), 8.06 (m, 1H), 7.72 (d, 1H), 7.42-7.28 (m, 5H), 7.08 (d, 1H), 5.18 (br. s. 1H), 4.50 (s, 2H) | [MH+] 348; tr 1.47 mins | A |
| A22 | 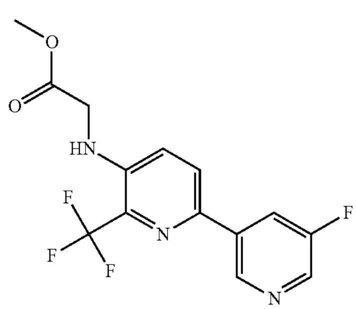 [SMILES: COC(=O)CNc1ccc(-c2cncc(F)c2)nc1C(F)(F)F] | 8.93 (s, 1H), 8.44 (d, 1H), 8.13-8.00 (m, 1H), 7.81 (d, 1H), 7.06 (d 1H), 5.34 (br. s, 1H), 4.03 (app. d, 2H), 3.85 (s, 3H) | [MH+] 330; tr 0.92 mins | B |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A23 | 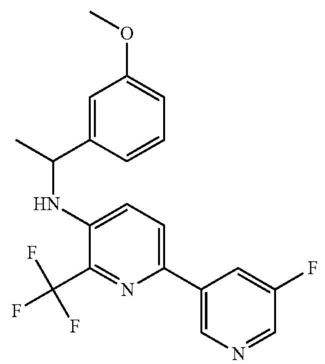 | 8.96 (s, 1H), 8.43 (d, 1H), 8.06 (m, 1H), 7.70 (d, 1H), 7.33-7.28 (m, 1H), 7.11 (d, 1H), 6.94-6.82 (m, 3H), 5.21 (br. s, 1H), 4.43, (s, 2H), 3.81 (s, 3H) | [MH+] 378; tr 1.46 mins | A |
| A24 | 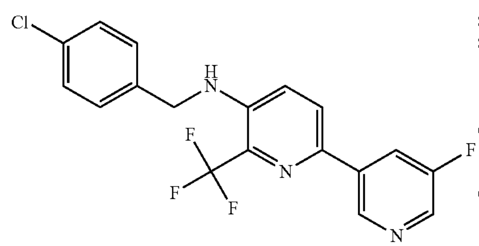 | 8.88 (s, 1H), 8.44-8.31 (m, 1H), 8.02 (m, 1H), 7.70 (d, 1H), 7.41-7.18 (m, 4H), 7.05 (d, 1H), 5.19 (br. s, 1H), 4.47 (app. d, 2H) | [MH+] 382; tr 1.23 mins | B |
| A25 | 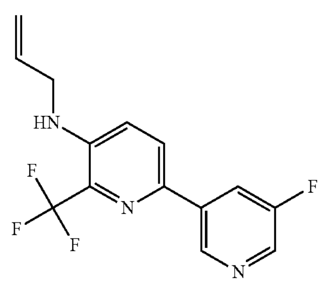 [SMILES: C=CCNc1ccc(-c2cncc(F)c2)nc1C(F)(F)F] | 8.92 (d, 1H), 8.42 (d, 1H), 8.05 (m, 1H), 7.78 (d, 1H), 7.16 (d, 1H), 5.99-5.88 (m, 1H), 5.37-5.23 (m, 2H), 4.85 (br. s, 1H), 3.97-3.88 (m, 2H) | [MH+] 298; tr 0.76 mins | C |
| A26 | 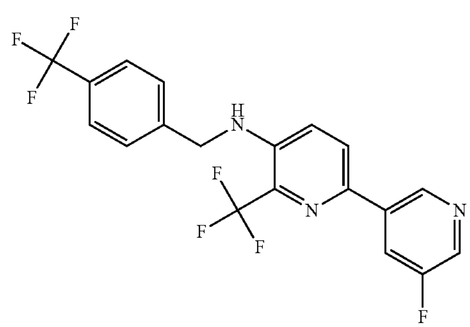 [SMILES: Fc1cncc(-c2ccc(NCc3ccc(C(F)(F)F)cc3)c(C(F)(F)F)n2)c1] | 8.95 (br. s, 1H), 8.48 (br. s, 1H), 8.06 (d, 1H), 7.72 (d, 1H), 7.65 (d, 2H), 7.46 (d, 2H), 7.02 (d, 1H), 5.26 (br. s, 1H), 4.58 (app. d, 2H) | [MH+] 416; tr 1.57 mins | A |
| A27 | 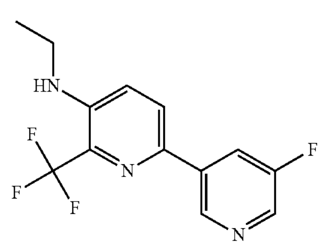 [SMILES: CCNc1ccc(-c2cncc(F)c2)nc1C(F)(F)F] | 8.93 (d, 1H), 8.42 (d, 1H), 8.08 (m, 1H), 7.79 (d, 1H), 7.17 (d, 1H), 4.63-4.46 (br. s, 1H), 3.28 (app. m, 2H), 1.35 (t, 3H) | [MH+] 286; tr 1.08 mins | B |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A28 | 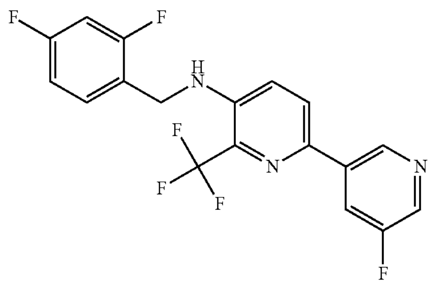 [SMILES: Fc1cncc(-c2ccc(NCc3ccc(F)cc3F)c(C(F)(F)F)n2)c1] | 8.90 (s, 1H), 8.42 (d, 1H), 8.03 (m, 1H), 7.75 (d, 1H), 7.37-7.24 (m, 1H), 7.13 (d, 1H), 6.88 (m, 2H), 5.13 (br. s, 1H), 4.51 app. d, 2H) | [MH+] 384; tr 1.22 mins | B |
| A29 | 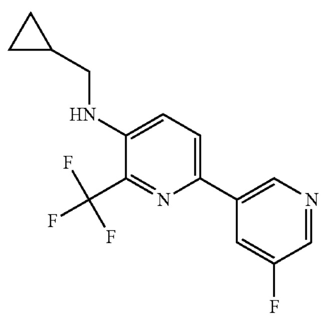 [SMILES: Fc1cncc(-c2ccc(NCC3CC3)c(C(F)(F)F)n2)c1] | 8.92 (s, 1H), 8.41 (d, 1H), 8.05 (m, 1H), 7.79 (d, 1H), 7.13 (d, 1H), 4.75 (br. s, 1H), 3.11-3.02 (m, 2H), 1.21-1.09 (m, 1H), 0.69-0.61 (m, 2H), 0.36-0.29 (m, 2H) | [MH+] 312; tr 0.83 mins | A |
| A30 | 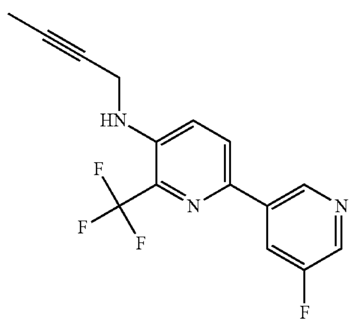 [SMILES: CC#CCNc1ccc(-c2cncc(F)c2)nc1C(F)(F)F] | 8.94 (s, 1H), 8.47 (s, 1H), 8.08 (m, 1H), 7.90 (d, 1H), 7.35 (d, 1H), 4.97-4.81 (br. s, 1H), 4.01 (br. m, 2H), 1.83 (dd, 3H) | [MH+] 310; tr 1.10 mins | B |
| A31 | 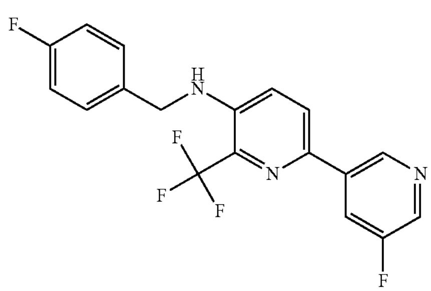 [SMILES: Fc1ccc(CNc2ccc(-c3cncc(F)c3)nc2C(F)(F)F)cc1] | 8.92 (s, 1H), 8.47 (d, 1H), 8.08 (m, 1H), 7.72 (m, 1H), 7.38-7.24 (m, 2H), 7.11-6.98 (m, 3H), 5.17 (br. s, 1H), 4.46 (s, 2H) | [MH+] 366; tr 1.49 mins | A |
| A32 | 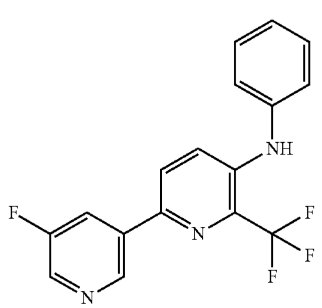 [SMILES: Fc1cncc(-c2ccc(Nc3ccccc3)c(C(F)(F)F)n2)c1] | 8.95 (s, 1H), 8.47 (d, 1H), 8.09 (m, 1H), 7.76 (d, 1H), 7.67 (d, 1H), 7.44-7.36 (m, 2H), 7.22-7.16 (m, 3H), 6.32 (br. s, 1H) | [MH+] 334; tr 1.21 mins | B |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A33 | 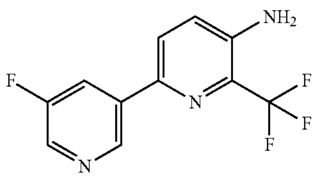 [SMILES: Nc1ccc(-c2cncc(F)c2)nc1C(F)(F)F] | 8.93 (m, 1H), 8.45 (d, 1H), 8.12-8.00 (m, 1H), 7.75 (d 1H), 7.21 (d, 1H), 4.38 (br. s, 2H) | | |
| A34 | 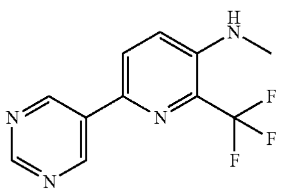 [SMILES: CNc1ccc(-c2cncnc2)nc1C(F)(F)F] | 9.28 (s, 2H), 9.19 (s, 1H), 7.80 (d, 1H), 7.19 (d, 1H), 4.77 (br. s, 1H), 2.98 (app. d, 3H) | [MH+] 255; tr 0.69 mins | B |
| A35 | 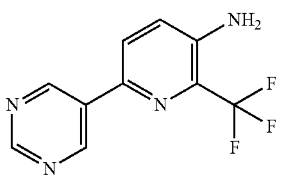 [SMILES: Nc1ccc(-c2cncnc2)nc1C(F)(F)F] | 9.28 (s, 2H), 9.21 (s, 1H), 7.74 (d, 1H), 7.23 (d, 1H), 4.43 (br. s, 2H) | [MH+] 279; tr 0.64 mins | A |
| A36 | 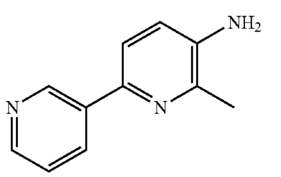 | 9.10 (s, 1H), 8.53 (d, 1H), 8.43 (m, 1H), 7.45 (d, 1H), 7.37-7.31 (m, 1H), 7.00 (d, 1H), 3.72 (br. s, 2H), 2.50 (s, 3H) | | |
| A38 | 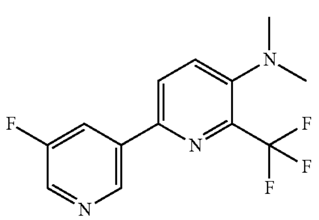 [SMILES: CN(C)c1ccc(-c2cncc(F)c2)nc1C(F)(F)F] | 8.97 (s, 1H), 8.48 (s, 1H), 8.12 (dt, 1H), 7.85 (d, 1H), 7.61 (d, 1H), 2.90 (s, 6H) | | |
| A39 | 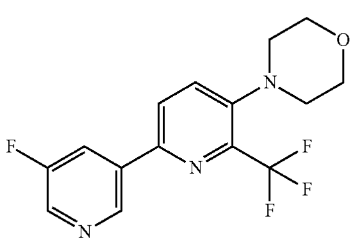 [SMILES: Fc1cncc(-c2ccc(N3CCOCC3)c(C(F)(F)F)n2)c1] | 9.00 (s, 1H), 8.51 (d, 1H), 8.16-8.11 (m, 1H), 7.93 (d, 1H), 7.74 (d, 1H), 3.92-3.86 (m, 4H), 3.07-3.00 (m, 4H). | | |
| A40 | 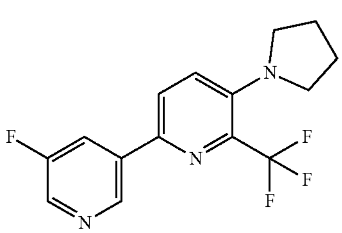 [SMILES: Fc1cncc(-c2ccc(N3CCCC3)c(C(F)(F)F)n2)c1] | 8.95 (s, 1H), 8.43 (d, 1H), 8.13-8.08 (m, 1H), 7.75 (d, 1H), 7.29 (d, 1H), 3.50-3.45 (m, 4H), 2.06-2.01 (m, 4H). | | |

TABLE 2-continued

Characterising data for Compounds of formula (I) made by the methods described above.

| Cmpd ID | Structure | $^1$H NMR Data (400 MHz, CDCl$_3$ unless stated) | m/z | method |
|---|---|---|---|---|
| A41 | 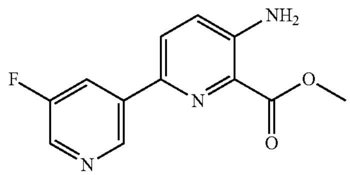 [SMILES: COC(=O)c1nc(-c2cncc(F)c2)ccc1N] | (2:1 d4-MeOH:d6-DMSO) 9.08 (s, 1H), 8.51 (d, 1H), 8.26-8.23 (m, 1H), 8.00 (d, 1H), 7.41 (d, 1H), 3.95 (s, 3H) | | |
| A42 | 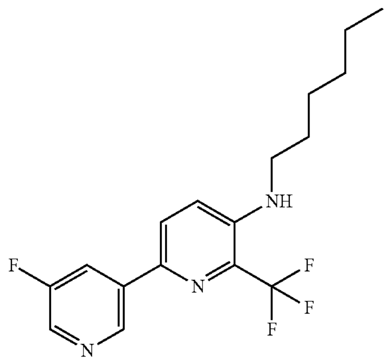 [SMILES: CCCCCCNc1ccc(-c2cncc(F)c2)nc1C(F)(F)F] | 8.94 (s, 1H), 8.43 (d, 1H), 8.09-8.03 (m, 1H), 7.80 (d, 1H), 7.18 (d, 1H), 4.61 (br. s, 1H), 3.26-3.19 (m, 2H), 1.75-1.66 (m, 2H), 1.49-1.32 (m, 6H), 0.96-0.89 (m, 3H) | | |
| A43 | 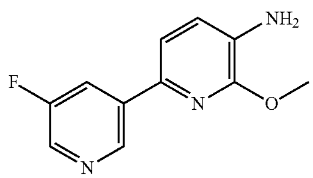 [SMILES: COc1nc(-c2cncc(F)c2)ccc1N] | 9.0 (s, 1H), 8.35 (s, 1H), 8.00 (dd, 1H), 7.25 (s, 1H), 6.90 (d, 1H), 4.10 (s, 3H), 4.00 (br. s, 2H) | | |
| A44 | 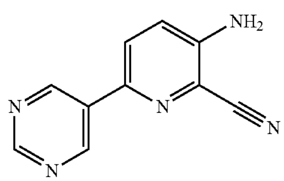 [SMILES: N#Cc1nc(-c2cncnc2)ccc1N] | (CD$_3$OD) 9.24 (s, 2H), 9.19 (s, 1H), 7.73 (d, 1H), 7.26 (d, 1H) | | |
| A45 | 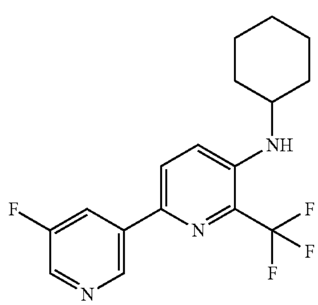 [SMILES: Fc1cncc(-c2ccc(NC3CCCCC3)c(C(F)(F)F)n2)c1] | 9.00 (s, 1H), 8.48 (d, 1H), 8.30-8.27 (m, 1H), 7.79 (d, 1H), 7.19 (d, 1H), 4.61 (br. s, 1H), 3.55-3.29 (m, 1H), 2.08-2.01 (m, 2H), 1.85-1.76 (m, 2H), 1.73-1.64 (m, 1H), 1.50-1.25 (m, 5H). | | |
| A46 | 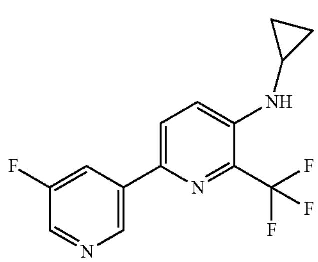 [SMILES: Fc1cncc(-c2ccc(NC3CC3)c(C(F)(F)F)n2)c1] | 8.99 (s, 1H), 8.47 (d, 1H), 8.21-8.16 (m, 1H), 7.85 (d, 1H), 7.65 (d, 1H), 5.08, (br. s, 1H), 2.59-2.51 (m, 1H), 0.96-0.89 (m, 2H), 0.68-0.61 (m, 2H) | | |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A47 | 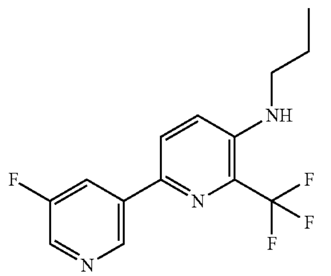 [SMILES: CCCNc1ccc(-c2cncc(F)c2)nc1C(F)(F)F] | 8.92 (s, 1H), 8.42 (d, 1H), 8.08-8.02 (m, 1H), 7.78 (d, 1H), 7.17 (d, 1H), 4.63 (br. s, 1H), 3.20 (dt, 2H), 1.76-1.67 (m, 2H), 1.05 (t, 3H) | | |
| A48 | 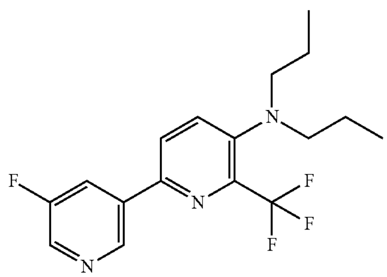 [SMILES: CCCN(CCC)c1ccc(-c2cncc(F)c2)nc1C(F)(F)F] | 8.99 (t, 1H), 8.49 (d, 1H), 8.17-8.11 (m, 1H), 7.87 (d, 1H), 7.71 (d, 1H), 3.09-3.02 (m, 4H), 1.57-1.45 (m, 4H), 0.87 (t, 6H) | | |
| A49 | 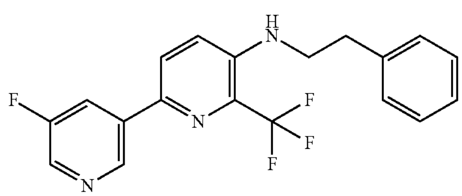 [SMILES: Fc1cncc(-c2ccc(NCCc3ccccc3)c(C(F)(F)F)n2)c1] | 8.91 (s, 1H), 8.41 (d, 1H), 8.08-8.00 (m, 1H), 7.77 (d, 1H), 7.38-7.32 (m, 2H), 7.30-7.22 (m, 3H), 7.17 (d, 1H), 4.69 (br. s, 1H), 3.52-3.45 (m, 2H), 2.99 (t, 2H) | | |
| A50 | 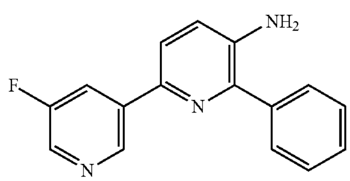 [SMILES: Nc1ccc(-c2cncc(F)c2)nc1-c1ccccc1] | 8.97 (s, 1H), 8.41 (d, 1H), 8.12-8.07 (m, 1H), 7.79-7.75 (m, 2H), 7.59 (d, 1H), 7.56-7.50 (m, 2H), 7.48-7.42 (m, 1H), 7.16 (d, 1H), 4.05 (br. s, 2H). | | |
| A51 | 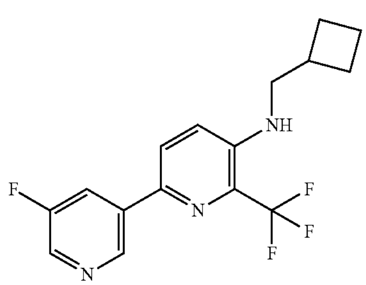 [SMILES: Fc1cncc(-c2ccc(NCC3CCC3)c(C(F)(F)F)n2)c1] | 8.92 (s, 1H), 8.42 (d, 1H), 8.08-8.01 (m, 1H), 7.78 (d, 1H), 7.16 (d, 1H), 4.54 (br. s, 1H), 3.23 (dd, 2H), 2.66 (m, 1H), 2.22-2.10 (m, 2H), 2.04-1.87 (m, 2H), 1.85-1.73 (m, 2H) | | |

TABLE 2-continued

Characterising data for Compounds of formula (I) made by the methods described above.

| Cmpd ID | Structure | ¹H NMR Data (400 MHz, CDCl₃ unless stated) | m/z | method |
|---|---|---|---|---|
| A52 | 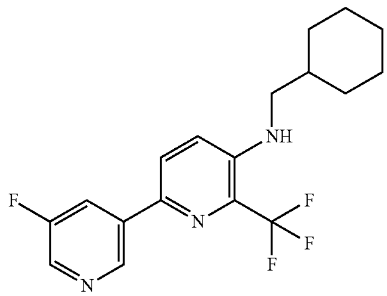 [SMILES: Fc1cncc(-c2ccc(NCC3CCCCC3)c(C(F)(F)F)n2)c1] | 8.92 (t, 1H), 8.42 (d, 1H), 8.09-8.01 (m, 1H), 7.78 (d, 1H), 7.16 (d, 1H), 4.69 (br. s, 1H), 3.10-3.03 (m, 2H), 1.8-1.60 (m, 6H), 1.35-1.17 (m, 3H), 1.10-0.96 (m, 2H) | | |
| A53 | 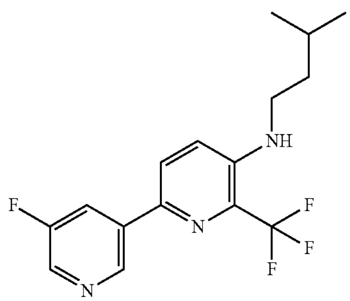 [SMILES: CC(C)CCNc1ccc(-c2cncc(F)c2)nc1C(F)(F)F] | 8.93 (t, 1H), 8.42 (d, 1H), 8.09-8.03 (m, 1H), 7.79 (d, 1H), 7.17 (d, 1H), 4.56 (br. s, 1H), 3.23 (dt, 2H), 1.82-1.67 (m, 1H), 1.60 (q, 2H), 0.99 (d, 6H) | | |
| A54 | 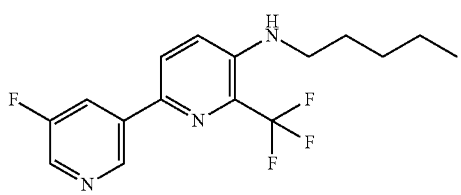 [SMILES: CCCCCNc1ccc(-c2cncc(F)c2)nc1C(F)(F)F] | 8.93 (t, 1H), 8.42 (d, 1H), 8.08-8.02 (m, 1H), 7.79 (d, 1H), 7.17 (d, 1H), 4.60 (br. s, 1H), 3.22 (dt, 2H), 1.76-1.64 (m, 2H), 1.45-1.34 (m, 4H), 0.98-0.91 (m, 3H) | | |
| A55 | 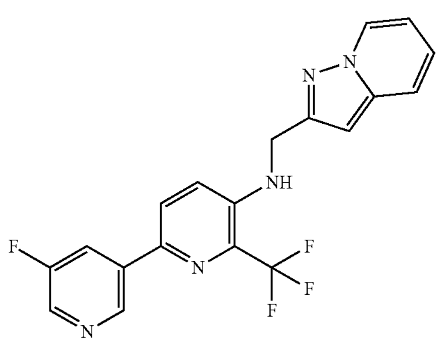 [SMILES: Fc1cncc(-c2ccc(NCc3cc4ccccn4n3)c(C(F)(F)F)n2)c1] | 8.91 (t, 1H), 8.46-8.39 (m, 2H), 8.10-8.00 (m, 1H), 7.76 (d, 1H), 7.47 (td, 1H), 7.29 (d, 1H), 7.12 (ddd, 1H), 6.77 (dt, 1H), 6.44 (s, 1H), 5.42 (br. s, 1H), 4.68 (d, 2H) | | |
| A56 | 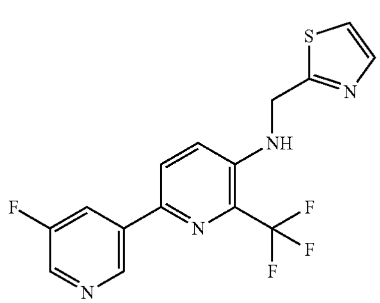 [SMILES: Fc1cncc(-c2ccc(NCc3nccs3)c(C(F)(F)F)n2)c1] | 8.92 (t, 1H), 8.44 (d, 1H), 8.09-8.01 (m, 1H), 7.81-7.74 (m, 2H), 7.33 (d, 1H), 7.28-7.25 (m, 1H), 5.58 (br. s, 1H), 4.83 (d, 2H) | | |

TABLE 2-continued

Characterising data for Compounds of formula (I) made by the methods described above.

| Cmpd ID | Structure | $^1$H NMR Data (400 MHz, CDCl$_3$ unless stated) | m/z | method |
|---|---|---|---|---|
| A57 | 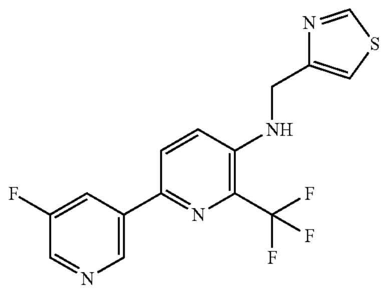 [SMILES: Fc1cncc(-c2ccc(NCc3cscn3)c(C(F)(F)F)n2)c1] | 8.92 (t, 1H), 8.86 (d, 1H), 8.43 (d, 1H), 8.09-8.02 (m, 1H), 7.77 (d, 1H), 7.25-7.19 (m, 2H), 5.41 (br. s, 1H), 4.68 (d, 2H) | | |
| A59 | 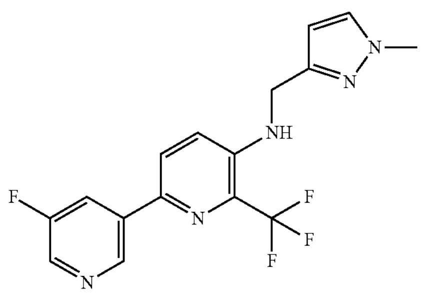 [SMILES: Cn1ccc(CNc2ccc(-c3cncc(F)c3)nc2C(F)(F)F)n1] | 8.92 (t, 1H), 8.42 (d, 1H), 8.08-8.03 (m, 1H), 7.77 (d, 1H), 7.33 (d, 1H), 7.29 (d, 1H), 6.19 (d, 1H), 5.25 (br. s, 1H), 4.45 (d, 2H), 3.90 (s, 3H) | | |
| A60 | 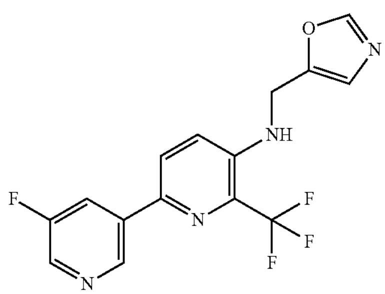 [SMILES: Fc1cncc(-c2ccc(NCc3cnco3)c(C(F)(F)F)n2)c1] | 8.93 (t, 1H), 8.45 (d, 1H), 8.09-8.03 (m, 1H), 7.88 (s, 1H), 7.82 (d, 1H), 7.29-7.25 (m, 1H), 7.05 (s, 1H), 5.06 (br. s, 1H), 4.56 (d, 2H) | | |
| A61 | 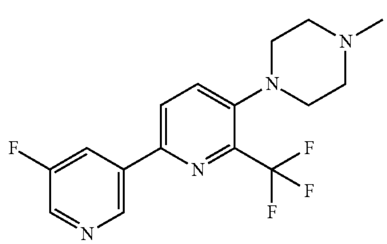 [SMILES: CN1CCN(c2ccc(-c3cncc(F)c3)nc2C(F)(F)F)CC1] | 9.02-8.99 (m, 1H), 8.52 (d, 1H), 8.17-8.12 (m, 1H), 7.93 (d, 1H), 7.76 (d, 1H), 3.09 (t, 4H), 2.69-2.59 (br. m, 4H), 2.40 (s, 3H) | | |
| A62 | 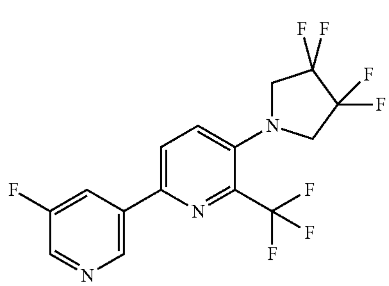 [SMILES: Fc1cncc(-c2ccc(N3CC(F)(F)C(F)(F)C3)c(C(F)(F)F)n2)c1] | 9.01 (s, 1H), 8.55-8.51 (m, 1H), 8.17-8.11 (m, 1H), 7.94 (d, 1H), 7.49 (d, 1H), 3.97-3.86 (m, 4H) | | |

TABLE 2-continued

Characterising data for Compounds of formula (I) made by the methods described above.

| Cmpd ID | Structure | $^1$H NMR Data (400 MHz, CDCl$_3$ unless stated) | m/z | method |
|---|---|---|---|---|
| A63 | 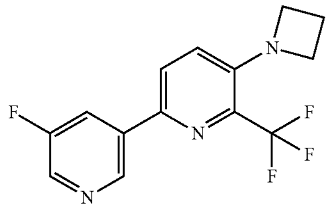 [SMILES: Fc1cncc(-c2ccc(N3CCC3)c(C(F)(F)F)n2)c1] | 8.94 (s, 1H), 8.43 (d, 1H), 8.11-8.05 (m, 1H), 7.76 (d, 1H), 6.92 (d, 1H), 4.18 (t, 4H), 2.43 (m, 2H) | | |
| A64 | 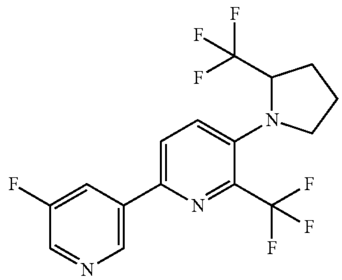 [SMILES: Fc1cncc(-c2ccc(N3CCCC3C(F)(F)F)c(C(F)(F)F)n2)c1] | 9.01 (s, 1H), 8.52 (d, 1H), 8.18-8.12 (m, 1H), 7.91 (d, 1H), 7.75 (d, 1H), 4.40-4.30 (m, 1H), 3.78-3.70 (m, 1H), 3.21-3.13 (m, 1H), 2.42-2.31 (m, 1H), 2.25-2.08 (m, 2H), 2.05-1.94 (m, 1H) | | |
| A65 | 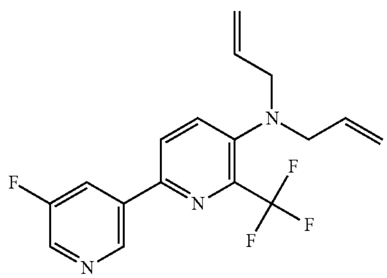 [SMILES: C=CCN(CC=C)c1ccc(-c2cncc(F)c2)nc1C(F)(F)F] | 9.00 (s, 1H), 8.49 (d, 1H), 8.19-8.12 (m, 1H), 7.89 (d, 1H), 7.69 (d, 1H), 5.89-5.76 (m, 2H), 5.22-5.11 (m, 4H), 3.69 (d, 4H) | | |
| A66 | 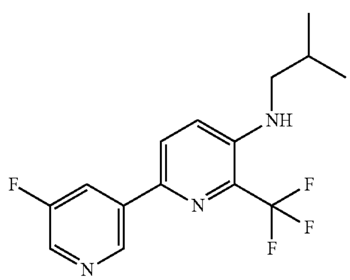 [SMILES: CC(C)CNc1ccc(-c2cncc(F)c2)nc1C(F)(F)F] | 8.91 (s, 1H), 8.41 (s, 1H), 8.04 (d, 1H), 7.77 (d, 1H), 7.15 (d, 1H), 4.70 (br. s, 1H), 3.06 (t, 2H), 1.97 (m, 1H), 1.03 (d, 6H) | | |
| A67 | 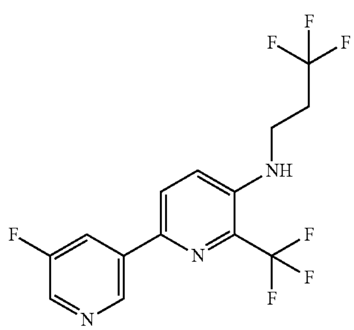 [SMILES: Fc1cncc(-c2ccc(NCCC(F)(F)F)c(C(F)(F)F)n2)c1] | 8.96 (s, 1H), 8.45 (s, 1H), 8.07 (d, 1H), 7.84 (d, 1H), 7.20 (d, 1H), 4.82 (br. s, 1H), 3.58 (m, 2H), 2.53 (m, 2H), | | |

Physical Characterisation

Compounds of the invention were characterised using one or more of the following methods.

NMR

NMR spectra contained herein were recorded on either a 400 MHz Bruker AVANCE III HD equipped with a Bruker SMART probe or a 500 MHz Bruker AVANCE III equipped with a Bruker Prodigy probe. Chemical shifts are expressed as ppm downfield from TMS, with an internal reference of either TMS or the residual solvent signals. The following multiplicities are used to describe the peaks: s=singlet, d=doublet, t=triplet, dd=double doublet, m=multiplet. Additionally br. is used to describe a broad signal and app. is used to describe and apparent multiplicity.

LCMS

LCMS data contained herein consists of the molecular ion [MH+] and the retention time (tr) of the peak recorded on the chromatogram. The following instruments, methods and conditions were used to obtain LCMS data:

Method A

Instrumentation:
Waters Acquity UPLC-MS using a Sample Organizer with Sample Manager FTN, H-Class QSM, Column Manager, 2×Column Manager Aux, Photodiode Array (Wavelength range (nm): 210 to 400, ELSD and SQD 2 equipped with a Waters HSS T3 C18 column (column length 30 mm, internal diameter of column 2.1 mm, particle size 1.8 micron).

Ionisation Method:
Electrospray positive and negative: Capillary (kV) 3.00, Cone (V) 30.00, Source Temperature (° C.) 500, Cone Gas Flow (L/Hr.) 10, Desolvation Gas Flow (L/Hr.) 1000. Mass range (Da): positive 95 to 800, negative 115 to 800.

The analysis was conducted using a two minute run time, according to the following gradient table at 40° C.:

| Time (mins) | Solvent A (%) | Solvent B (%) | Flow (ml/mm) |
|---|---|---|---|
| 0.00 | 95.0 | 5.0 | 0.7 |
| 1.75 | 0.0 | 100 | 0.7 |
| 1.76 | 0.0 | 100 | 0.7 |
| 2.0 | 0.0 | 5.0 | 0.7 |
| 2.01 | 95.0 | 5.0 | 0.7 |
| 2.11 | 95.0 | 5.0 | 0.7 |

Solvent A: $H_2O$ with 0.05% TFA
Solvent B: $CH_3CN$ with 0.05% TFA

Method B (2 min Method)

Instrumentation:
Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

L C-Method:
Phenomenex 'Kinetex C18 100A' column (50 mm×4.6 mm, particle size 2.6 micron),
Flow rate: 2 mL/min at 313K (40 Celsius),
Gradient (Solvent A: $H_2O$ with 0.1% Formic Acid; Solvent B: Acetonitrile with 0.1% Formic Acid):

The analysis was conducted using a two minute run time, according to the following gradient table at 40° C.

| Time (mins) | Solvent A (%) | Solvent B (%) | Flow (ml/mm) |
|---|---|---|---|
| Initial | 70.0 | 30.0 | 2.000 |
| 1.20 | 10.0 | 90.0 | 2.000 |
| 1.70 | 10.0 | 90.0 | 2.000 |
| 1.80 | 70.0 | 30.0 | 2.000 |
| 2.00 | 70.0 | 30.0 | 2.000 |
| 2.20 | 70.0 | 30.0 | 2.000 |

Method C (1 min Method)

Instrumentation:
Either (a) Waters Acquity UPLC system with Waters SQD2 single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash); or (b) Waters Acquity UPLC system with Waters QDa single-quad MS detector, Photodiode Array Detector (Absorbance Wavelength: 254 nm, 10 pts/sec, Time Constant: 0.2000 sec), Charged Aerosol Detector (Corona) and Waters CTC 2770 auto-sampler unit (injection volume: 2 microliters, 1 min seal wash).

L C-Method:
Phenomenex 'Kinetex C18 100A' column (50 mm×4.6 mm, particle size 2.6 micron),
Flow rate: 2 mL/min at 313K (40 Celsius),
Gradient (Solvent A: $H_2O$ with 0.1% Formic Acid; Solvent B: Acetonitrile with 0.1% Formic Acid):

The analysis was conducted using a one minute run time, according to the following gradient table at 40° C.

| Time (mins) | Solvent A (%) | Solvent B (%) | Flow (ml/mm) |
|---|---|---|---|
| Initial | 60.0 | 40.0 | 2.000 |
| 0.80 | 0.0 | 100.0 | 2.000 |
| 0.95 | 0.0 | 100.0 | 2.000 |
| 1.00 | 60.0 | 40.0 | 2.000 |
| 1.10 | 60.0 | 40.0 | 2.000 |
| 1.25 | 60.0 | 40.0 | 2.000 |

BIOLOGICIAL EXAMPLES

B1 Pre-Emergence Herbicidal Activity

Seeds of a variety of test species were sown in standard soil in pots: Triticum aestivium (TRZAW), Avena fatua (AVEFA), Alopecurus myosuroides (ALOMY), Echinochloa crus-galli (ECHCG), Lolium perenne (LOLPE), Zea Mays (ZEAMX), Abutilon theophrasti (ABUTH), Amaranthus retroflexus (AMARE) and Setaria faberi (SETFA). After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B1a and B1b.

Tables B1a and B1b Control of Weed Species by Compound of Formula (I) after Pre-Emergence Application TABLE B1a Test 1a

| Compound ID | Rate (g/ha) | LOLPE | SETFA | ALOMY | ECHCG | AVEFA | TRAZW |
|---|---|---|---|---|---|---|---|
| A1 | 1000 | 1 | 4 | 0 | 1 | 1 | 0 |
| A2 | 1000 | 1 | 4 | 0 | 2 | 0 | 0 |
| A3 | 1000 | 1 | 5 | 0 | 3 | 1 | 0 |
| A4 | 1000 | 1 | 2 | 0 | 1 | 0 | 0 |
| A38 | 1000 | 0 | 5 | 0 | 5 | 2 | 0 |
| A39 | 1000 | 0 | 3 | 0 | 3 | 0 | 0 |
| A40 | 1000 | 1 | 4 | 1 | 4 | 1 | 0 |
| A41 | 1000 | 0 | 2 | 0 | 2 | 0 | 0 |
| A42 | 1000 | 1 | 5 | 0 | 4 | 2 | 0 |
| A43 | 1000 | 1 | 1 | 0 | 0 | 0 | 0 |
| A44 | 1000 | 2 | 5 | 0 | 3 | 1 | 0 |
| A45 | 1000 | 0 | 4 | 0 | 3 | 1 | NT |
| A46 | 1000 | 0 | 4 | 0 | 2 | 1 | 0 |
| A47 | 1000 | 1 | 4 | 0 | 3 | 1 | 0 |
| A48 | 1000 | 0 | 4 | 0 | 4 | 0 | 0 |
| A49 | 1000 | 1 | 5 | 0 | 3 | 1 | 0 |
| A50 | 1000 | 0 | 1 | 0 | 1 | 0 | 0 |
| A51 | 1000 | 1 | 5 | 1 | 5 | 1 | 1 |
| A52 | 1000 | 1 | 5 | 0 | 3 | 1 | 0 |
| A53 | 1000 | 2 | 5 | 1 | 4 | 1 | 1 |
| A54 | 1000 | 1 | 5 | 0 | 3 | 1 | 0 |
| A55 | 1000 | 1 | 5 | 0 | 5 | 2 | 0 |
| A56 | 1000 | 1 | 5 | 0 | 4 | 2 | 1 |
| A57 | 1000 | 1 | 5 | 1 | 5 | 3 | 0 |
| A59 | 1000 | 1 | 5 | 0 | 4 | 3 | 0 |
| A60 | 1000 | 1 | 5 | 0 | 5 | 3 | 0 |
| A61 | 1000 | 0 | 5 | 0 | 4 | 2 | 0 |
| A62 | 1000 | 0 | 5 | 0 | 3 | 1 | 0 |
| A63 | 1000 | 0 | 5 | 0 | 2 | 0 | 0 |
| A64 | 1000 | 0 | 1 | 0 | 1 | 0 | 0 |

TABLE B1b

Test 1b

| Compound ID | Rate (g/ha) | LOLPE | AMARE | SETFA | ECHCG | ZEAMX | ABUTH |
|---|---|---|---|---|---|---|---|
| A5 | 1000 | 1 | 2 | 5 | 2 | 4 | 1 |
| A6 | 1000 | 0 | 1 | 1 | 0 | 0 | 1 |
| A7 | 1000 | 0 | 1 | 3 | 0 | 0 | 1 |
| A8 | 1000 | 1 | 0 | 5 | 2 | 3 | 0 |
| A9 | 1000 | 0 | 1 | 4 | 4 | 2 | 1 |
| A10 | 1000 | 0 | 1 | 2 | 0 | 1 | 1 |
| A11 | 1000 | 1 | 1 | 5 | 2 | 1 | 1 |
| A12 | 1000 | 0 | 0 | 0 | 0 | 0 | 0 |
| A13 | 1000 | 0 | 0 | 0 | 0 | 0 | 0 |
| A14 | 1000 | 1 | 0 | 2 | 1 | 1 | 0 |
| A15 | 1000 | 0 | 0 | 1 | 1 | 1 | 0 |
| A16 | 1000 | 0 | 0 | 4 | 1 | 1 | 0 |
| A17 | 1000 | 0 | 0 | 2 | 0 | 0 | 0 |
| A18 | 1000 | 0 | 0 | 4 | 2 | 4 | 0 |
| A19 | 1000 | 2 | 1 | 4 | 3 | 5 | 0 |
| A20 | 1000 | 0 | 0 | 5 | 2 | 3 | 0 |
| A21 | 1000 | 2 | 1 | 5 | 3 | 3 | 0 |
| A22 | 1000 | 2 | 3 | 4 | 4 | 5 | 0 |
| A23 | 1000 | 0 | 0 | 4 | 1 | 2 | 0 |
| A24 | 1000 | 1 | 0 | 4 | 2 | 3 | 0 |
| A25 | 1000 | 2 | 1 | 4 | 4 | 5 | 0 |
| A26 | 1000 | 0 | 0 | 4 | 2 | 2 | 0 |
| A27 | 1000 | 2 | 0 | 4 | 5 | 5 | 0 |
| A28 | 1000 | 0 | 0 | 4 | 2 | 2 | 0 |
| A29 | 1000 | 3 | 3 | 5 | 4 | 5 | 1 |
| A30 | 1000 | 2 | 2 | 5 | 4 | 5 | 0 |
| A31 | 1000 | 2 | 1 | 5 | 4 | 4 | 1 |
| A32 | 1000 | 1 | 1 | 5 | 4 | 1 | 1 |

TABLE B1b-continued

| Compound ID | Rate (g/ha) | LOLPE | AMARE | SETFA | ECHCG | ZEAMX | ABUTH |
|---|---|---|---|---|---|---|---|
| A33 | 1000 | 2 | 1 | 4 | 2 | 4 | 0 |
| A34 | 1000 | 3 | 1 | 4 | 4 | 4 | 0 |
| A35 | 1000 | 2 | 1 | 4 | 3 | 5 | 0 |
| A36 | 1000 | 0 | 1 | 1 | 0 | 0 | 1 |

B2 Post-Emergence Herbicidal Activity

Seeds of a variety of test species were sown in standard soil in pots: *Triticum* aestivium (TRZAW), *Avena fatua* (AVEFA), *Alopecurus myosuroides* (ALOMY), *Echinochloa crus-galli* (ECHCG), *Lolium perenne* (LOLPE), *Zea Mays* (ZEAMX), *Abutilon theophrasti* (ABUTH), *Amaranthus retroflexus* (AMARE) and *Setaria faberi* (SETFA). After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Tables B2a and B2b.

Tables B2a and B2b Control of Weed Species by Compound of Formula (I) after Post-Emergence Application

TABLE B2a

| Compound ID | Rate (g/ha) | LOLPE | SETFA | ALOMY | ECHCG | AVEFA | TRAZW |
|---|---|---|---|---|---|---|---|
| A1 | 1000 | 2 | 5 | 0 | 3 | 3 | 2 |
| A2 | 1000 | 2 | 5 | 1 | 4 | 3 | 0 |
| A3 | 1000 | 2 | 4 | 1 | 3 | 3 | 0 |
| A4 | 1000 | 1 | 4 | 1 | 2 | 3 | 1 |
| A38 | 1000 | 2 | 5 | 1 | 5 | 4 | 1 |
| A39 | 1000 | 2 | 4 | 0 | 4 | 2 | 0 |
| A40 | 1000 | 2 | 5 | 0 | 5 | 3 | 0 |
| A41 | 1000 | 0 | 2 | 0 | 2 | 1 | 0 |
| A42 | 1000 | 2 | 5 | 1 | 5 | 3 | 1 |
| A43 | 1000 | 1 | 2 | 0 | 1 | 1 | 0 |
| A44 | 1000 | 1 | 4 | 0 | 3 | 2 | 0 |
| A45 | 1000 | 1 | 4 | 0 | 2 | 2 | 0 |
| A46 | 1000 | 2 | 4 | 1 | 4 | 3 | 1 |
| A47 | 1000 | 2 | 5 | 0 | 4 | 2 | 2 |
| A48 | 1000 | 2 | 5 | 0 | 4 | 3 | 1 |
| A49 | 1000 | 3 | 5 | 0 | 3 | 3 | 0 |
| A50 | 1000 | 0 | 2 | 0 | 1 | 0 | 0 |
| A51 | 1000 | 3 | 4 | 1 | 5 | 4 | 2 |
| A52 | 1000 | 3 | 5 | 0 | 3 | 3 | 0 |
| A53 | 1000 | 3 | 5 | 1 | 5 | 3 | 1 |
| A54 | 1000 | 2 | 5 | 0 | 3 | 3 | 0 |
| A55 | 1000 | 3 | 5 | 1 | 5 | 4 | 2 |
| A56 | 1000 | 3 | 5 | 1 | 5 | 4 | 1 |
| A57 | 1000 | 4 | 5 | 1 | 5 | 4 | 2 |
| A59 | 1000 | 3 | 5 | 1 | 5 | 3 | 2 |
| A60 | 1000 | 4 | 5 | 1 | 5 | 3 | 2 |
| A61 | 1000 | 2 | 5 | 1 | 5 | 3 | 1 |
| A62 | 1000 | 2 | 5 | 0 | 3 | 3 | 0 |
| A63 | 1000 | 2 | 5 | 0 | 3 | 3 | 0 |
| A64 | 1000 | 0 | 4 | 0 | 2 | 1 | 0 |

TABLE B2b

| Compound ID | Rate (g/ha) | LOLPE | AMARE | SETFA | ECHCG | ZEAMX | ABUTH |
|---|---|---|---|---|---|---|---|
| A5 | 1000 | 4 | 1 | 5 | 4 | 5 | 1 |
| A6 | 1000 | 1 | 0 | 3 | 1 | 1 | 0 |
| A7 | 1000 | 1 | 1 | 3 | 1 | 1 | 0 |
| A8 | 1000 | 3 | 0 | 5 | 4 | 5 | 0 |
| A9 | 1000 | 1 | 1 | 4 | 4 | 4 | 1 |
| A10 | 1000 | 1 | 1 | 3 | 1 | 2 | 0 |
| A11 | 1000 | 4 | 1 | 5 | 4 | 2 | 1 |

TABLE B2b-continued

Test B2b

| Compound ID | Rate (g/ha) | LOLPE | AMARE | SETFA | ECHCG | ZEAMX | ABUTH |
|---|---|---|---|---|---|---|---|
| A12 | 1000 | 0 | 0 | 1 | 1 | 1 | 0 |
| A13 | 1000 | 0 | 1 | 1 | 1 | 2 | 0 |
| A14 | 1000 | 1 | 2 | 3 | 2 | 2 | 0 |
| A15 | 1000 | 1 | 1 | 2 | 2 | 1 | 0 |
| A16 | 1000 | 1 | 0 | 5 | 3 | 3 | 0 |
| A17 | 1000 | 1 | 0 | 4 | 4 | 4 | 0 |
| A18 | 1000 | 2 | 0 | 5 | 3 | 5 | 0 |
| A19 | 1000 | 3 | 2 | 5 | 4 | 5 | 1 |
| A20 | 1000 | 2 | 0 | 5 | 3 | 5 | 0 |
| A21 | 1000 | 1 | 1 | 5 | 1 | 5 | 0 |
| A22 | 1000 | 4 | 3 | 5 | 5 | 5 | 2 |
| A23 | 1000 | 2 | 0 | 5 | 2 | 5 | 0 |
| A24 | 1000 | 2 | 0 | 5 | 3 | 5 | 0 |
| A25 | 1000 | 3 | 2 | 5 | 4 | 5 | 0 |
| A26 | 1000 | 2 | 0 | 4 | 3 | 5 | 0 |
| A27 | 1000 | 4 | 0 | 5 | 4 | 5 | 0 |
| A28 | 1000 | 2 | 1 | 5 | 3 | 5 | 0 |
| A29 | 1000 | 4 | 2 | 5 | 5 | 5 | 2 |
| A30 | 1000 | 4 | 2 | 5 | 5 | 5 | 2 |
| A31 | 1000 | 3 | 1 | 5 | 4 | 5 | 0 |
| A32 | 1000 | 3 | 0 | 5 | 4 | 4 | 0 |
| A33 | 1000 | 3 | 2 | 5 | 3 | 5 | 1 |
| A34 | 1000 | 3 | 2 | 5 | 5 | 5 | 1 |
| A35 | 1000 | 4 | 2 | 5 | 4 | 5 | 1 |
| A36 | 1000 | 1 | 1 | 2 | 1 | 2 | 0 |

The invention claimed is:

1. A compound of Formula (I-i)

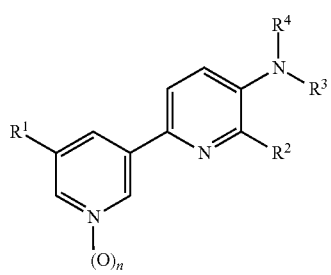

or a salt thereof, wherein:

$R^1$ is selected from the group consisting of hydrogen, cyano, fluoro, chloro, methoxy-, difluoromethoxy, and trifluoromethyl;

$R^2$ is selected from the group consisting of halogen, cyano, nitro, $C_1$-$C_6$alkyl, $C_1$-$C_6$haloalkyl, $C_2$-$C_6$alkenyl, $C_2$-$C_6$alkynyl, $C_3$-$C_6$cycloalkyl, —C(O)OC$_1$-$C_6$alkyl, —S(O)$_p$($C_1$-$C_6$alkyl), $C_1$-$C_6$alkoxy, $C_1$-$C_6$haloalkoxy and phenyl;

$R^3$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^a$ is hydrogen or $C_1$-$C_2$ alkyl;

$R^b$ is hydrogen or $C_1$-$C_2$ alkyl;

$R^4$ is selected from the group consisting of hydrogen, $C_1$-$C_6$alkyl, $C_2$-$C_6$alkenyl, $C_2$-$C_6$alkynyl, $C_2$-$C_6$haloalkenyl, $C_1$-$C_6$alkoxyC$_1$-$C_3$alkyl-, $C_1$-$C_6$haloalkyl- and —(CR$^a$R$^b$)$_q$R$^5$;

$R^5$ is —C(O)OC$_1$-$C_6$alkyl, —$C_3$-$C_{10}$cycloalkyl, -aryl and -heteroaryl wherein said aryl and heteroaryl are optionally substituted by 1 to 3 independent $R^8$;

or $R^3$ and $R^4$ together with the nitrogen to which they are attached, form a saturated or partially unsaturated 4-6 membered ring system optionally containing 1 or 2 further heteroatoms independently selected from S, O and N, wherein said ring is optionally substituted by 1 to 3 $R^8$;

$R^6$ and $R^7$ are independently selected from the group consisting of hydrogen and $C_1$-$C_6$alkyl;

each $R^8$ is independently selected from the group consisting of halogen, $C_1$-$C_6$ alkyl and $C_1$-$C_6$alkoxy-, $C_1$-$C_6$ haloalkyl, $C_1$-$C_6$ haloalkoxy-, cyano and S(O)$_p$($C_1$-$C_6$alkyl);

n is 0 or 1;

p is 0, 1, or 2;

and q is 0, 1, or 2;

with the proviso that:

(a) $R^3$ and $R^4$ are not both H, when $R^2$ is methyl, n is 0, and $R^1$ is methoxy, H, fluoro, or cyano; and (b) the compound of formula (Ia) is not (i) 2-chloro-6-(3-pyridyl)pyridine-3-amine, (ii) 2-fluoro-6-(3-pyridyl)pyridine-3-amine, (iii) 2-(difluoromethyl)-6-(3- pyridyl)pyridin-3-amine, or (iv) tert-butyl-N-[2-methyl- 6-(3-pyridyl)-3- pyridyl]-carbamate.

2. The compound of formula (I-i) according to claim 1, wherein $R^2$ is $C_1$-$C_6$alkyl, $C_1$-$C_6$haloalkyl, cyano, —C(O)OC$_1$-$C_6$alkyl, $C_1$-$C_6$alkoxy, or phenyl.

3. The compound of formula (I-i) according to claim 1, wherein $R^3$ is selected from the group consisting of hydrogen, $C_1$-$C_6$alkyl, $C_2$-$C_6$alkenyl, $C_2$-$C_6$alkynyl, and (CR$^a$R$^b$)$_q$R$^5$.

4. The compound of formula (I-i) according to claim 1, wherein $R^3$ is selected from the group consisting of hydrogen, $C_1$-$C_6$alkyl, $C_2$-$C_6$alkenyl, $C_2$-$C_6$alkynyl, phenyl, benzyl, —(CH$_2$)C$_3$-$C_{10}$cycloalkyl, —CH(CH$_3$)phenyl, —CH$_2$C(O)OC$_1$-$C_6$alkyl, and —CH—(CH$_3$)C(O)OC$_1$-$C_6$alkyl, wherein said benzyl and phenyl are optionally substituted by one to three independent $R^8$.

5. The compound of formula (I-i) according to claim 1, wherein $R^4$ is hydrogen.

6. The compound of formula (I-i) according to claim 1, wherein $R^3$ and $R^4$ together with the nitrogen atom to which they are joined, form a saturated or partially unsaturated 5- or 6-membered ring system optionally containing from 1 or 2 further heteroatoms independently selected from S, O and N, wherein said ring is optionally substituted by 1 to 3 independent $R^8$.

7. The compound of formula (I-i) according to claim 6, wherein $R^3$ and $R^4$ together with the nitrogen atom to which they are joined form a pyrrolinyl, pyrrolidinyl, pyrazolinyl, pyrazolidinyl, imidazolinyl, imidazolidinyl, triazolyl, piperidyl, morpholinyl, thiomorpholinyl, and piperazinyl ring, each optionally substituted by 1 to 3 independent $R^8$.

8. The compound of formula (I-i) according to claim 2, wherein $R^3$ is selected from the group consisting of hydrogen, $C_1$-$C_6$alkyl, $C_2$-$C_6$alkenyl, $C_2$-$C_6$alkynyl, and $(CR^aR^b)_qR^5$.

9. The compound of formula (I-i) according to claim 8, wherein $R^1$ is flourine.

10. The compound of formula (I-i) according to claim 9, wherein $R^4$ is hydrogen.

11. The compound of formula (I-i) according to claim 10, wherein $R^2$ is trifluoromethyl, methyl, or cyano.

12. The compound of formula (I-i) according to claim 2, wherein $R^3$ is selected from the group consisting of hydrogen, $C_1$-$C_6$alkyl, $C_2$-$C_6$alkenyl, $C_2$-$C_6$alkynyl, phenyl, benzyl, —(CH$_2$)C$_3$-C$_{10}$cycloalkyl, —CH(CH$_3$)phenyl, —CH$_2$C(O)OC$_1$-C$_6$alkyl, and —CH—(CH$_3$)C(O)OC$_1$-C$_6$alkyl, wherein said benzyl and phenyl are optionally substituted by one to three independent $R^8$.

13. The compound of formula (I-i) according to claim 2, wherein the compound is selected from the group consisting of:

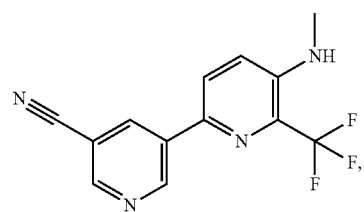

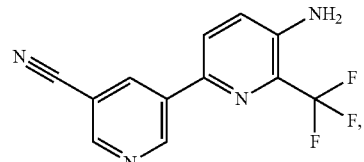

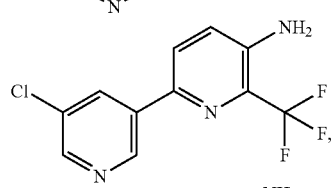

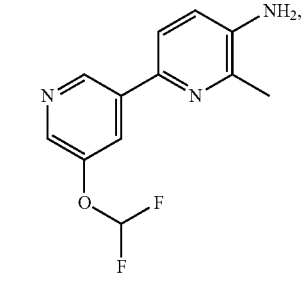

-continued

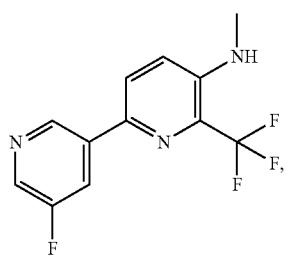

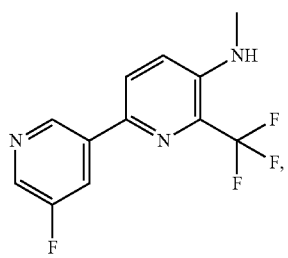

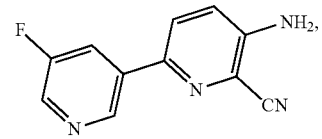

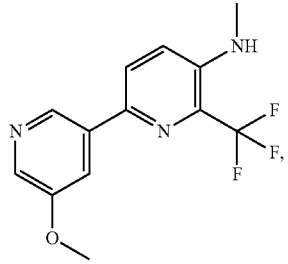

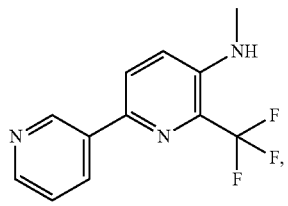

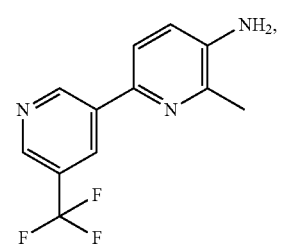

77
-continued
78
-continued
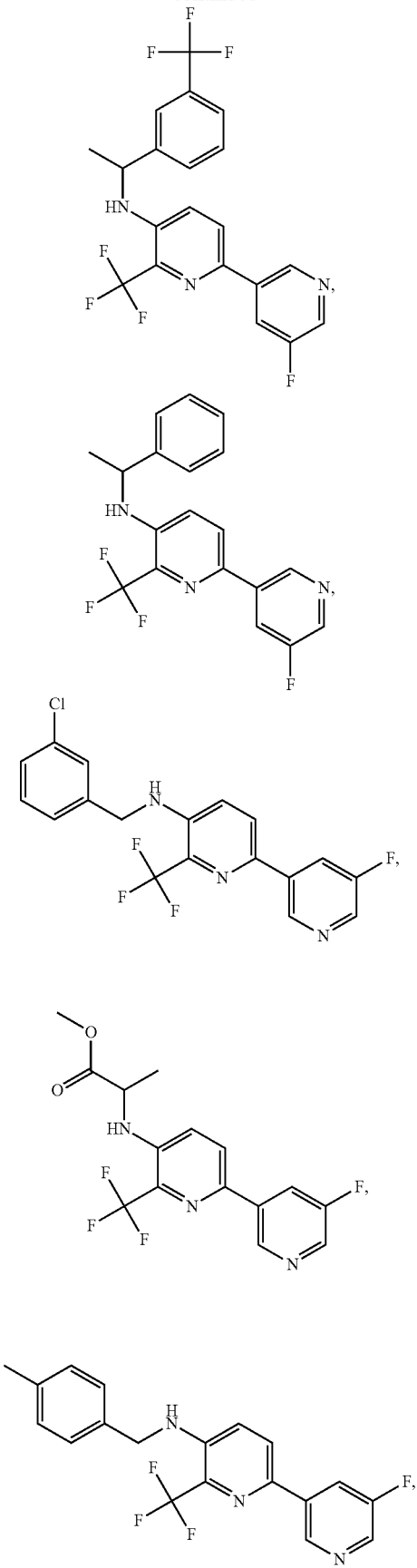
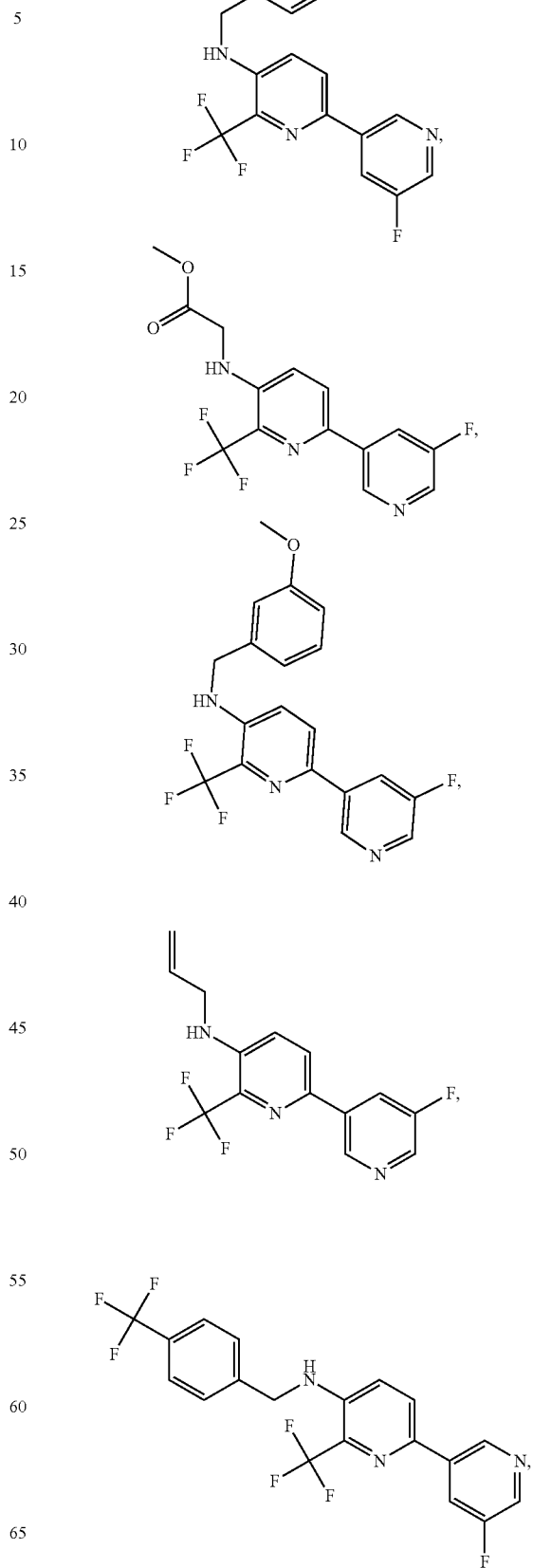

-continued
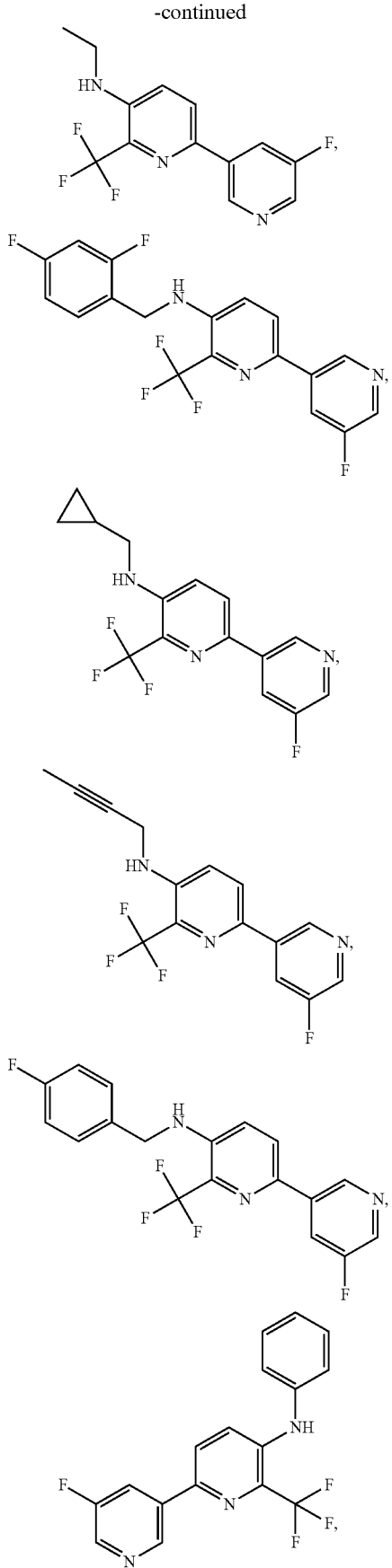
-continued
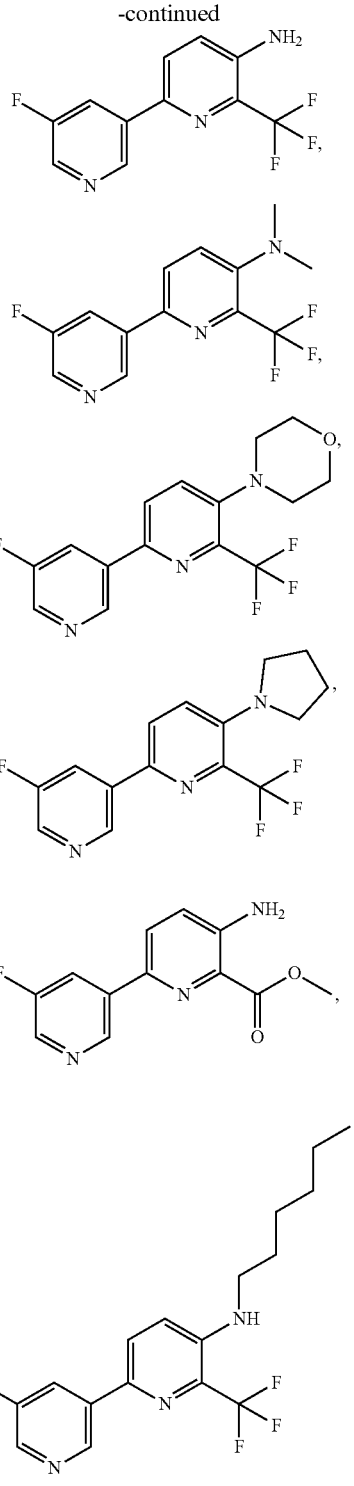

-continued
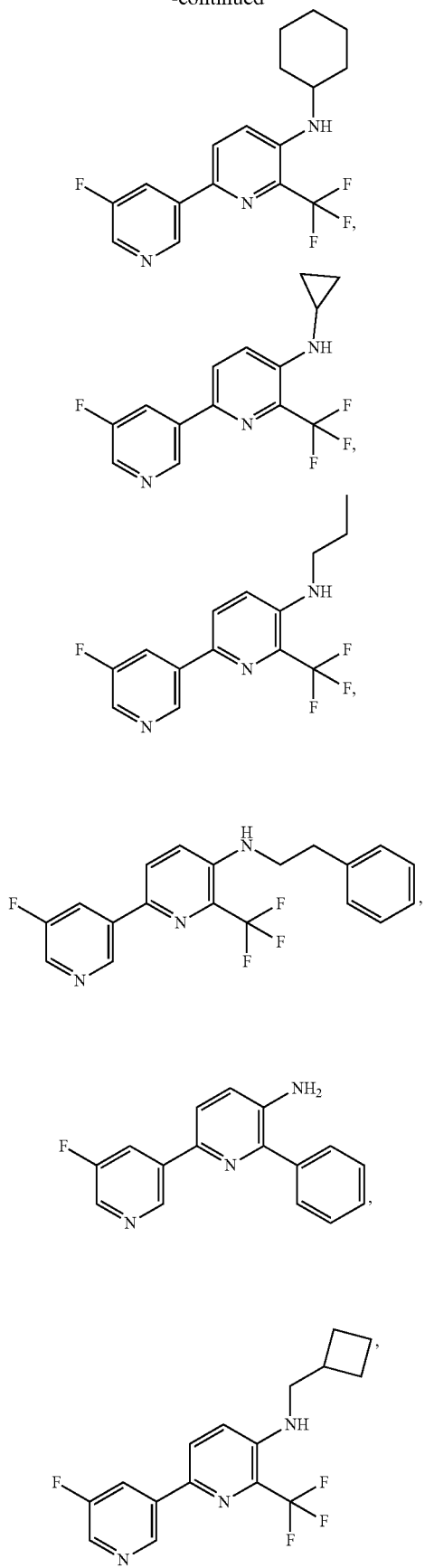
-continued
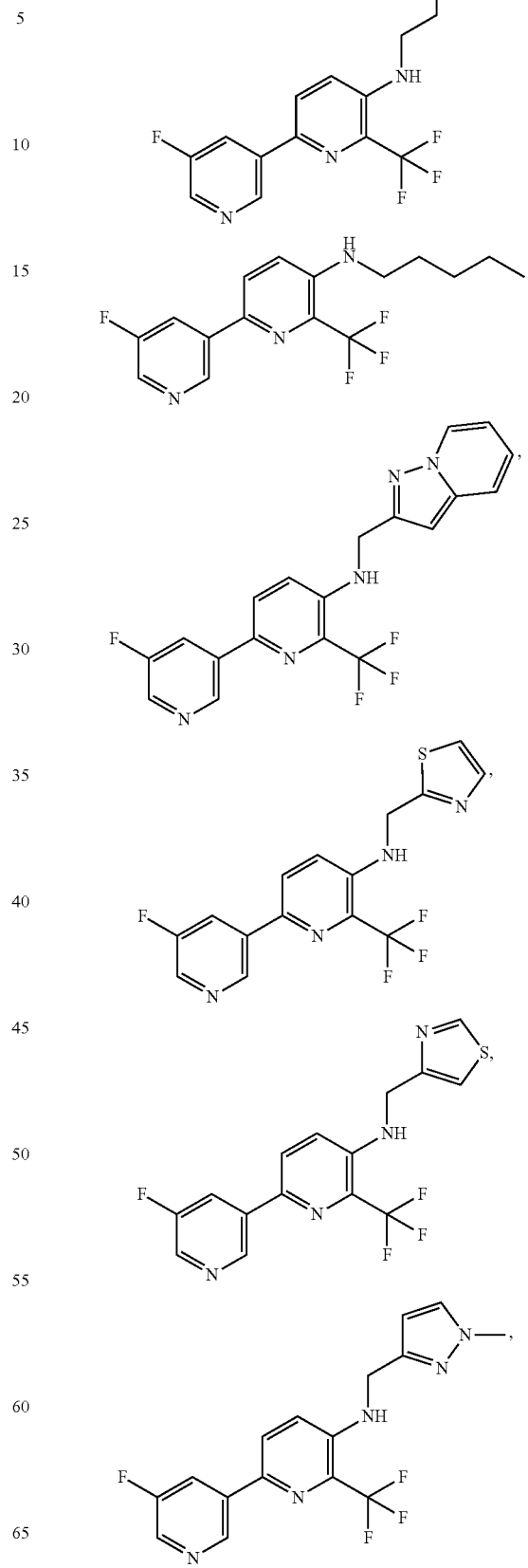

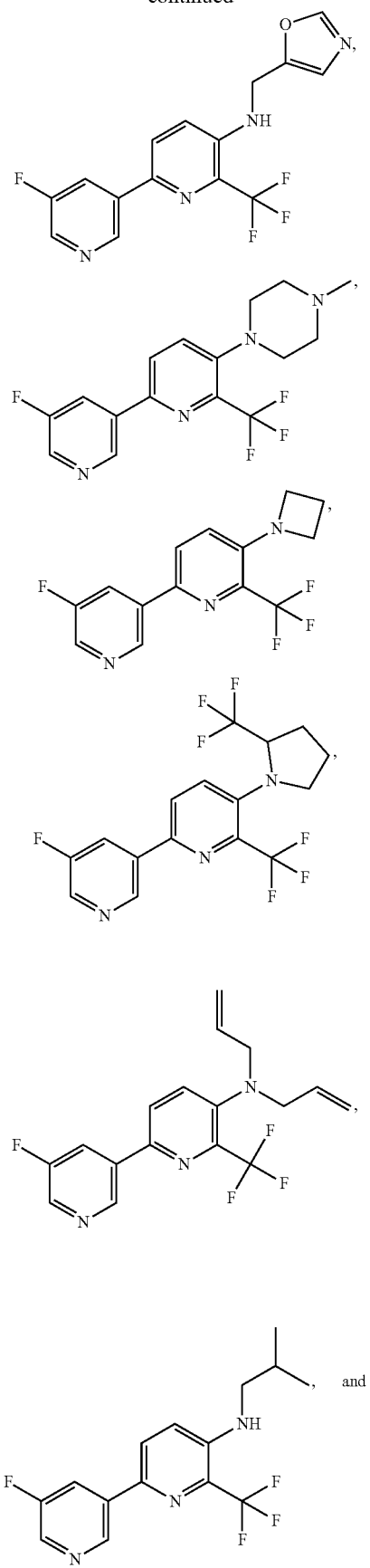
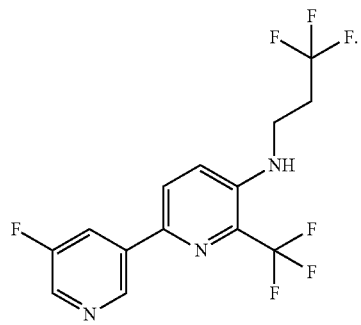
14. The compound of formula (I-i) according to claim 13, wherein the compound is selected from the group consisting of:

-continued
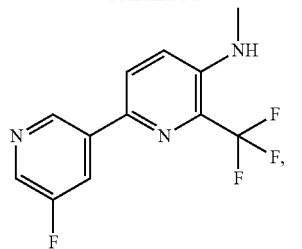
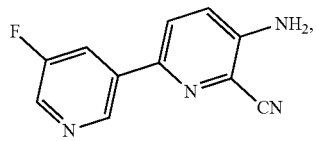
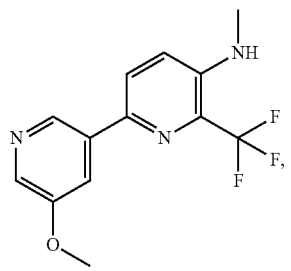
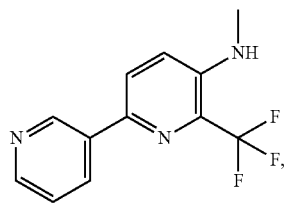
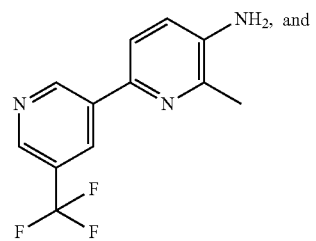
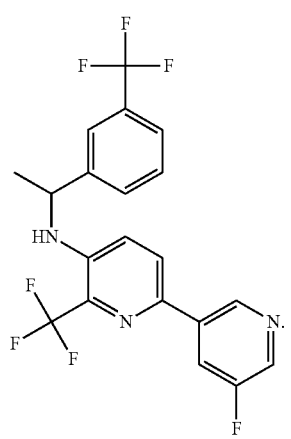
15. The compound of formula (I-i) according to claim 13, wherein the compound is selected from the group consisting of:
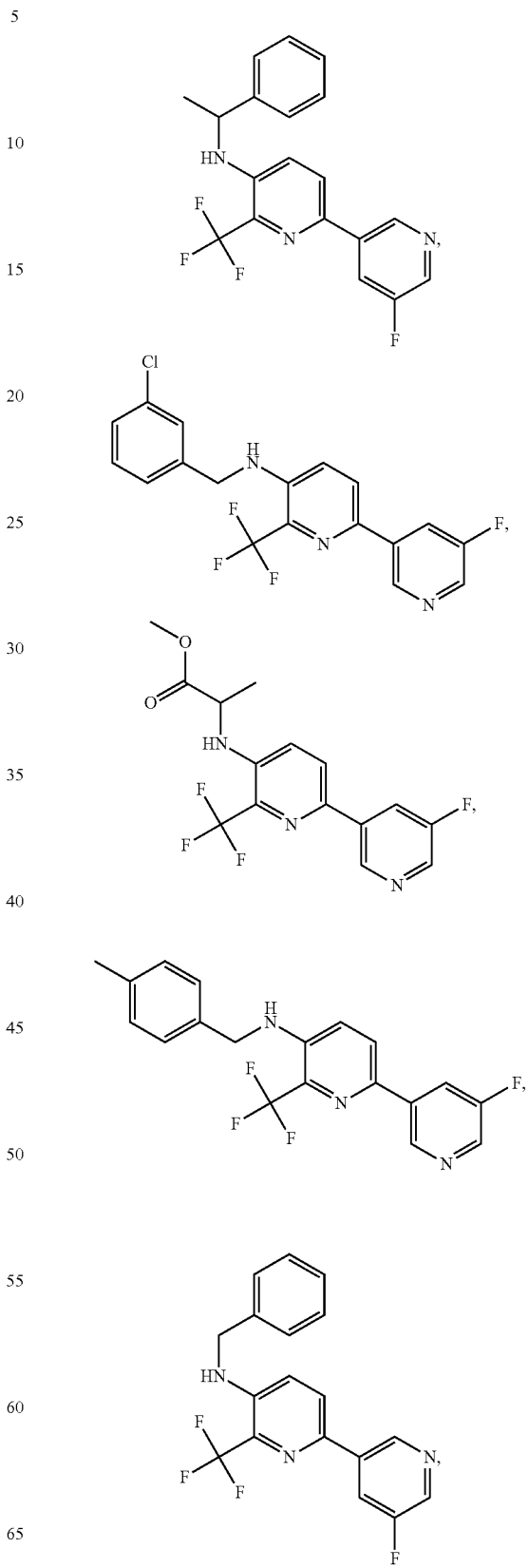

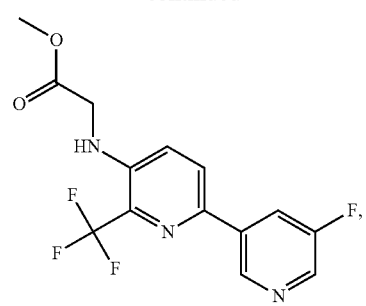
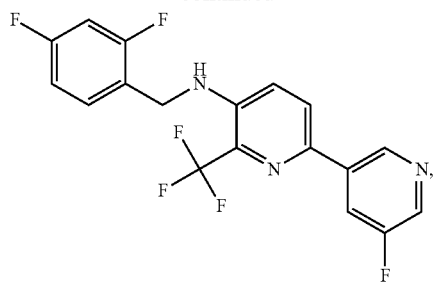
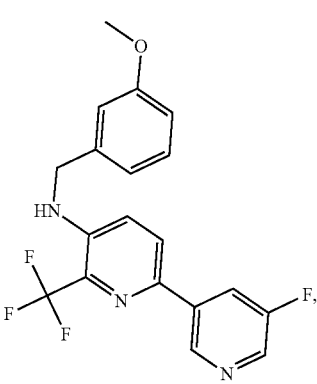
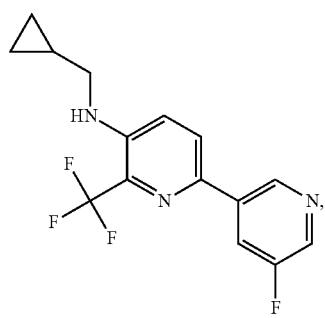
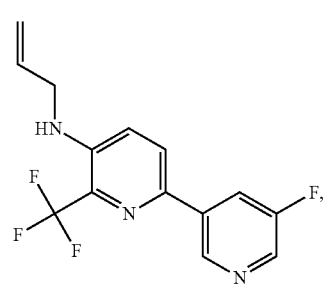
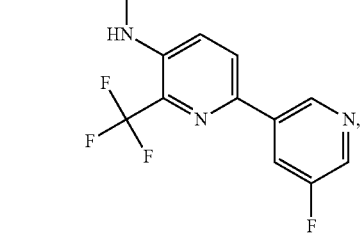
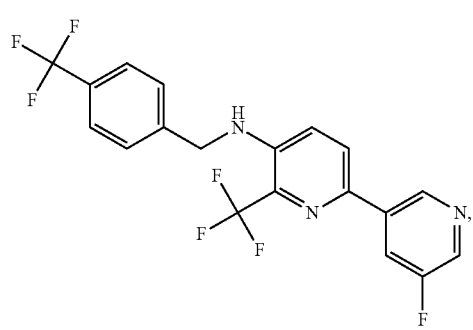
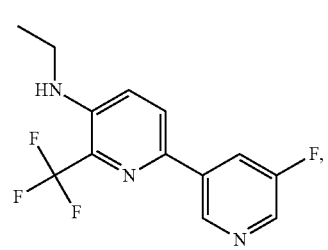
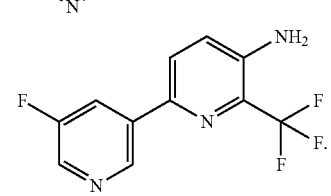

16. The compound of formula (I-i) according to claim 13, wherein the compound is selected from the group consisting of:
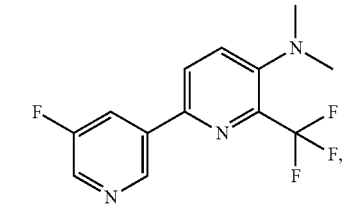
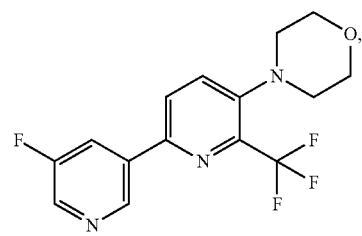
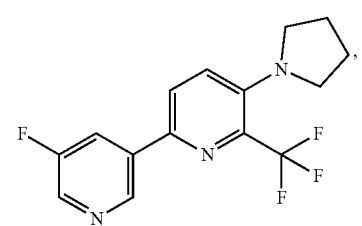
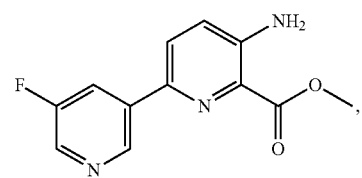
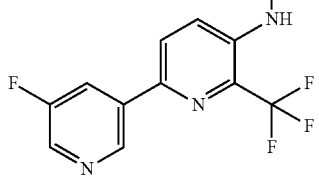
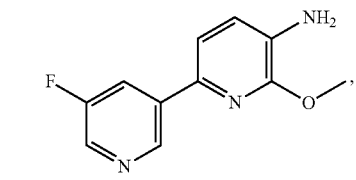
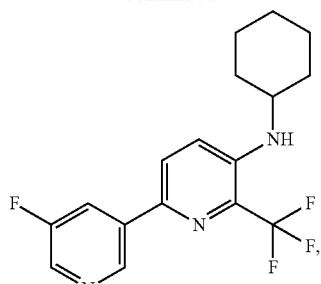
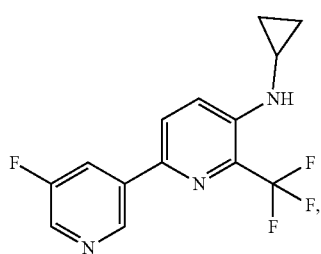
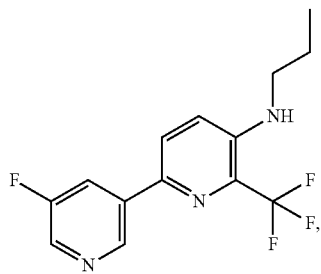
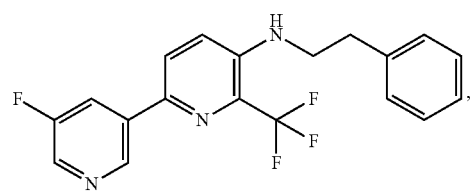
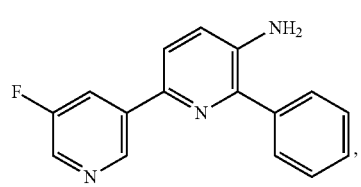
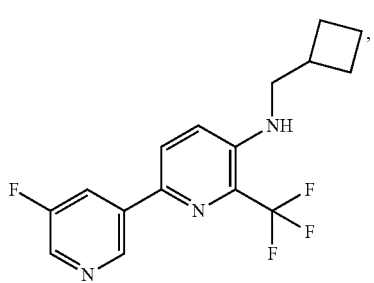

-continued
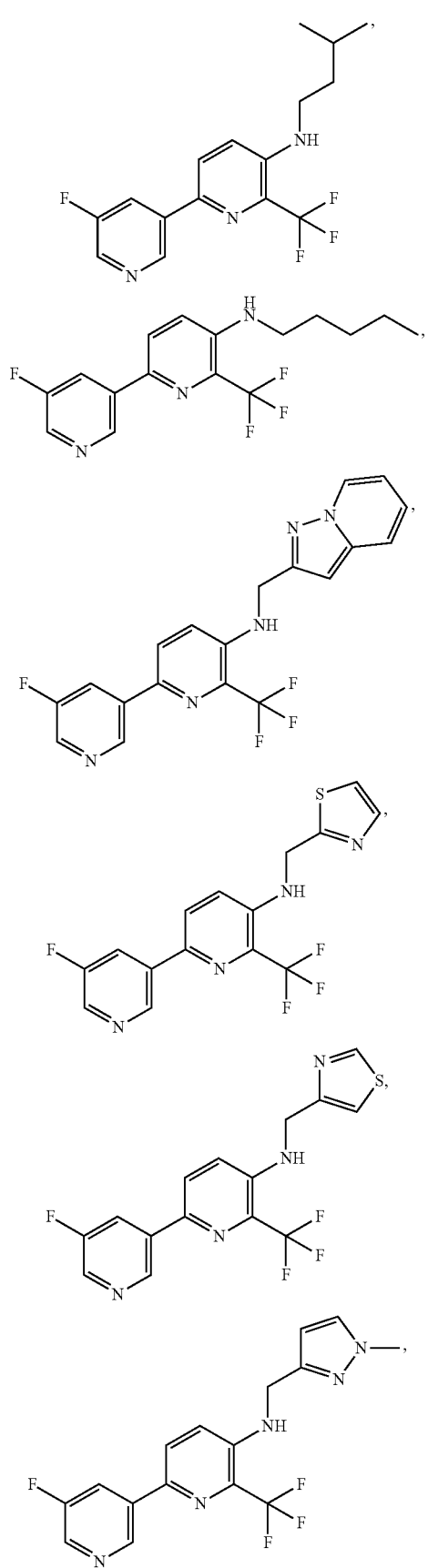
-continued
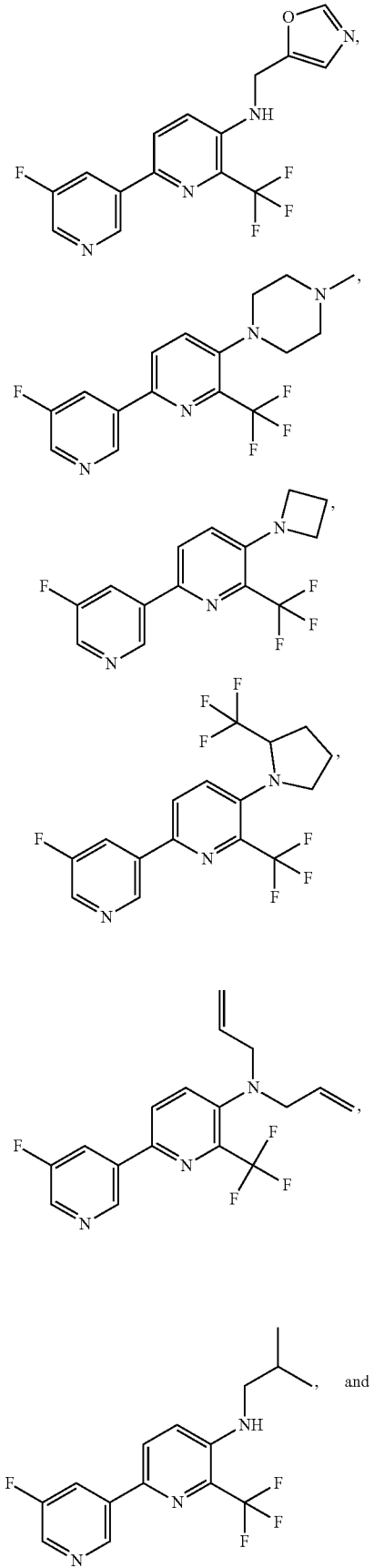

-continued
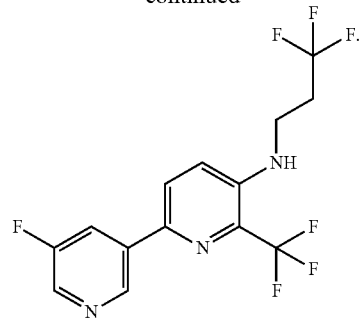
* * * * *